(12) United States Patent
Ouwerkerk

(10) Patent No.: US 8,633,695 B2
(45) Date of Patent: Jan. 21, 2014

(54) ADIABATIC MULTI-BAND RF PULSES FOR SELECTIVE SIGNAL SUPPRESSION IN A MAGNETIC RESONANCE IMAGING

(75) Inventor: Ronald Ouwerkerk, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 384 days.

(21) Appl. No.: 13/057,903

(22) PCT Filed: Aug. 13, 2009

(86) PCT No.: PCT/US2009/053739
§ 371 (c)(1),
(2), (4) Date: Feb. 7, 2011

(87) PCT Pub. No.: WO2010/019790
PCT Pub. Date: Feb. 18, 2010

(65) Prior Publication Data
US 2011/0144474 A1    Jun. 16, 2011

Related U.S. Application Data

(60) Provisional application No. 61/088,374, filed on Aug. 13, 2008.

(51) Int. Cl.
*G01V 3/00* (2006.01)

(52) U.S. Cl.
USPC ............................................ 324/309

(58) Field of Classification Search
USPC .................................. 324/300–322
See application file for complete search history.

(56) References Cited

U.S. PATENT DOCUMENTS

| | | | |
|---|---|---|---|
| 6,018,600 A | 1/2000 | Levin et al. | |
| 7,275,010 B2* | 9/2007 | Mitschang | 702/127 |
| 7,279,899 B2* | 10/2007 | Michaeli et al. | 324/318 |
| 7,683,618 B2* | 3/2010 | Balchandani et al. | 324/309 |
| 7,787,930 B2* | 8/2010 | Nezafat et al. | 600/410 |
| 7,932,719 B2* | 4/2011 | Liimatainen et al. | 324/307 |
| 8,324,898 B2* | 12/2012 | Sung et al. | 324/309 |
| 2006/0208730 A1 | 9/2006 | Kozerke et al. | |
| 2006/0224062 A1 | 10/2006 | Aggarwal et al. | |

OTHER PUBLICATIONS

International Search Report and Written Opinion for PCT/US2009/053739.
Bottomley PA, Andrew ER. RF magnetic field penetration, phase shift and power dissipation in biological tissue: implications for NMR imaging. Phys Med Biol 1978; 23(4):630-643.

(Continued)

*Primary Examiner* — Dixomara Vargas
(74) *Attorney, Agent, or Firm* — Venable LLP; Henry J. Daley

(57) ABSTRACT

A magnetic resonance imaging (MRI) system, comprising: a magnetic resonance imaging scanner comprising: a main magnet providing a substantially uniform main magnetic field B0 for a subject under observation; and a radio frequency (RF) coil configured to irradiate a radio frequency (RF) pulse into a region of interest of the subject under observation, wherein the RF pulse comprises a base pulse comprising an adiabatic pulse having a first bandwidth time product (BWTP), wherein the RF pulse selectively suppresses magnetic resonance signals from more than one chemical component or more than one spatial region within the region of interest of the subject under observation, and wherein the adiabatic pulse is characterized by an amplitude modulation function and a frequency modulation function.

30 Claims, 13 Drawing Sheets

(56) References Cited

OTHER PUBLICATIONS

Bottomley PA. Spatial localization in NMR spectroscopy in vivo. Ann N Y Acad Sci 1987;508:333-348.

DeGraaf RA, Nicolay K. Adiabatic rf pulses: Applications to in vivo NMR. Concept Magnetic Res 1997;9(4):247-268.

Edden RA, Barker PB. Spatial effects in the detection of gammaaminobutyric acid: Improved sensitivity at high fields using inner volume saturation. Magn Reson Med 2007;58(6):1276-1282.

Garwood M, DelaBarre L. The return of the frequency sweep: Designing adiabatic pulses for contemporary NMR. Journal of Magnetic Resonance 2001;153(2):155-177.

Goelman G. Fast Hadamard spectroscopic imaging techniques. J Magn Reson B 1994;104(3):212-218.

Goelman G. Hadamard encoding with surface coils for high SNR MR spectroscopy. Magn Reson Imaging 1999;17(5): 777-781.

Goelman G. Two methods for peak RF power minimization of multiple inversion-band pulses. Magn Reson Med 1997;37(5):658-665.

Hwang TL, van Zijl PCM, Garwood M. Asymmetric adiabatic pulses for NH selection. Journal of Magnetic Resonance 1999;138(1):173-177.

Kirkpatrick S, Gelatt CD, Jr., Vecchi MP. Optimization by Simulated Annealing. Science 1983;220(4598):671680.

Kupce E, Freeman R. Close Encounters between Soft Pulses. Journal of Magnetic Resonance Series A 1995;112(2):261-264.

Mescher M, Merkle H, Kirsch J, Garwood M, Gruetter R. Simultaneous in vivo spectral editing and water suppression. NMR in Biomedicine 1998;11(6):266-272.

Norris DG. Adiabatic radiofrequency pulse forms in biomedical nuclear magnetic resonance. Concept Magnetic Res 2002;14(2):89-101.

Ogg RJ, Kingsley PB, Taylor JS. Wet, a T-1-Insensitive and B-1-Insensitive Water-Suppression Method for in-Vivo Localized H-1-NMR Spectroscopy. Journal of Magnetic Resonance Series B 1994;104(1):1-10.

Ouwerkerk R, Edden RA. Multi-Band Adiabatic Pulses. Mar. 2006; Proc. Intl. Soc. Mag. Reson. Med. 14 Seattle, WA, USA. p. 3006.

Ouwerkerk R. Dual-Band Adiabatic Selective Refocussing for Signal Suppression in High Field MR. Proc 15th Meeting ISMRM; May 2007; Berlin, Germany. p. 1678.

Ouwerkerk R. Fast Sequence Optimization for Superior Signal Suppression with Multiple Hyperbolic Secant Pulses. Proc. 15th Meeting ISMRM; May 2007; Berlin, Germany. p. 1674. (Proc. 15th Meeting ISMRM)).

Patt SL. Single- and Multiple-Frequency-Shifted Laminar Pulses. Journal of Magnetic Resonance 1992;96:94-102.

Pauly J, Leroux P, Nishimura D, Macovski A. Parameter Relations for the Shinnar-Leroux Selective Excitation Pulse Design Algorithm. IEEE Transactions on Medical Imaging 1991;10(1):53-65.

Silver MS, Joseph RI, Hoult DI. Selective Spin Inversion in Nuclear Magnetic-Resonance and Coherent Optics through an Exact Solution of the Bloch-Riccati Equation. Phys Rev A 1985;31(4):2753-2755.

Steffen M, Vandersypen LMK, Chuang IL. Simultaneous soft pulses applied at nearby frequencies. Journal of Magnetic Resonance 2000;146(2):369-374.

Stuber M, Gilson WD, Schar M, Kedziorek DA, Hofmann LV, Shah S, Vonken EJ, Bulte JW, Kraitchman DL. Positive contrast visualization of iron oxide-labeled stem cells using inversion-recovery with ON-resonant water suppression (IRON). Magn Reson Med 2007;58(5):1072-1077.

Tannus A, Garwood M. Improved performance of frequency-swept pulses using offset-independent adiabaticity. J Magn Reson Ser A 1996;120(1):133-137.

Terpstra M, Gruetter R. 1H NMR detection of vitamin C in human brain in vivo. Magn Reson Med 2004;51(2):225-229.

Tkac I, Starcuk Z, Choi IY, Gruetter R. In vivo 1H NMR spectroscopy of rat brain at 1 ms echo time. Magn Reson Med 1999;41(4):649-656.

Tsekos NV, Garwood M, Merkle H, Xu Y, Wilke N, Ugurbil K. Myocardial Tagging with B-1 Insensitive Adiabatic Dante Inversion Sequences. Magnet Reson Med 1995;34(3):395-401.

Tsekos NV, Garwood M, Ugurbil K. Tagging of the magnetization with the transition zones of 360 degrees rotations generated by a tandem of two adiabatic DANTE inversion sequences. J Magn Reson 2002;156(2):187-194.

Ugurbil K, Garwood M, Rath AR. Optimization of Modulation Functions to Improve Insensitivity of Adiabatic Pulses to Variations in B1 Magnitude. Journal of Magnetic Resonance 1988;80(3):448-469.

\* cited by examiner

ADIABATIC MULTI-BAND RF PULSES FOR SELECTIVE SIGNAL SUPPRESSION IN A MAGNETIC RESONANCE IMAGING

CROSS-REFERENCE OF RELATED APPLICATION

This application claims priority to U.S. Provisional Application No. 61/088,374 filed Aug. 13, 2008, the entire contents of which are hereby incorporated by reference, and is a U.S. national stage application under 35 U.S.C. §of PCTUS2009/053739 filed Aug. 13, 2009, the entire contents of which are incorporated herein by reference.

The U.S. Government has a paid-up license in this invention and the right in limited circumstances to require the patent owner to license others on reasonable terms as provided for by the terms of Grant No.: R01CA100184, R21CA095907, P41RR15241 and R01RR015396 awarded by the National Institutes of Health.

BACKGROUND

1. Field of Invention

The current invention relates to magnetic resonance systems and more particularly to systems that provide adiabatic pulses.

2. Discussion of Related Art

Selective signal suppression is required in many Magnetic Resonance Imaging (MRI) and Magnetic Resonance Spectroscopy (MRS) scans. Usually the desired frequency-selection profile is made up of an excitation band with a constant effective flip-angle, flanked by transition bands that are as narrow as possible. Non-adiabatic pulses, such as the Shinnar-La Roux (SLR) pulses, can be specifically designed to achieve these goals, but desired profiles are achieved only in a narrow range of flip-angles (Pauly J, Leroux P, Nishimura D, Macovski A. Parameter Relations for the Shinnar-Leroux Selective Excitation Pulse Design Algorithm. IEEE Transactions on Medical Imaging 1991; 10(1):53-65). The frequency response profile of an SLR pulse designed for a 90° flip angle degrades when the flip angle is changed to 180°, meaning that a separate pulse shape has to be calculated. Depending on design parameters, sometimes SLR pulse profiles deteriorate even when flip angles are off by just ±30°. All non-adiabatic pulses suffer from similar variations in excitation profile at larger flip-angles. As a result, the use of these pulses for signal suppression require a careful calibration of RF power and RF excitation coil with a homogeneous RF field. With non-adiabatic pulses, a certain degree of on-resonance, $B_1$-independent response may be achieved when used in optimized multi-pulse saturation sequences, but the off-resonance profile degrades as $B_1$ values deviate from the design optimum. Thus, combinations of $B_1$ and $B_0$ inhomogeneity can seriously reduce the saturation efficiency. In high field magnets, this can be a serious problem, because localized shimming with higher-order shim coils will create more $B_0$ inhomogeneity outside the volume-of-interest (VOI). The resulting insufficient suppression of signals from around the VOI is likely to lead to artifacts in most MR experiments, commonly referred to as outer volume signals. In short, the utility of these pulse sequences at $B_0$ field strengths of 3 T and higher is often hampered by problems arising from power-deposition and $B_1$ inhomogeneity.

The radiofrequency (RF) power deposition, or Specific Absorption Rate (SAR), is intricately linked with the $B_1$ field inhomogeneity problem (Bottomley P A, Andrew E R. RF magnetic field penetration, phase shift and power dissipation in biological tissue: implications for NMR imaging. Phys Med Biol 1978; 23(4):630-643). The most obvious solution to problems arising from $B_1$ inhomogeneity is to use either larger coils with more uniform $B_1$ field, or adiabatic pulses that may be independent of $B_1$ field. Either solution increases the SAR and the required RF amplifier power. Further, the solution of using a large coil does not address issues of outer volume signal suppression or susceptibility (e.g., metal implants in knees and necks of patients). Conversely, attempts to reduce SAR by using smaller excitation coils usually lead to loss of $B_1$ field homogeneity.

Adiabatic pulses are amplitude- and frequency-modulated pulses that can achieve spatially uniform excitation, inversion, and/or refocusing when the transmitted RF power is over a threshold. Thus, adiabatic pulses can be insensitive to local $B_1$ field variations (DeGraaf R A, Nicolay K. Adiabatic rf pulses: Applications to in vivo NMR. Concept Magnetic Res 1997; 9(4):247-268, Norris D G. Adiabatic radiofrequency pulse forms in biomedical nuclear magnetic resonance. Concept Magnetic Res 2002; 14(2):89-101). With adiabatic pulses, the desired frequency-selection profile (an excitation band with a constant effective flip-angle, flanked by transition bands that are as narrow as possible) can be achieved more effectively than with most non-adiabatic pulses. Selective adiabatic pulses may achieve an excitation profile with hardly any variation over multi-fold changes in the $B_1$ field (Garwood M, DelaBarre L. The return of the frequency sweep: Designing adiabatic pulses for contemporary NMR. Journal of Magnetic Resonance 2001; 153(2): 155-177).

However, to date, few attempts have been made to create multi-band adiabatic pulses (Goelman G. Two methods for peak RF power minimization of multiple inversion-band pulses. Magn Reson Med 1997; 37(5):658-665, Tsekos N V, Garwood M, Ugurbil K. Tagging of the magnetization with the transition zones of 360 degrees rotations generated by a tandem of two adiabatic DANTE inversion sequences. J Magn Reson 2002; 156(2):187-194, Tsekos N V, Garwood M, Merkle H, Xu Y, Wilke N, Ugurbil K. Myocardial Tagging with B-1 Insensitive Adiabatic Dante Inversion Sequences. Magnet Reson Med 1995; 34(3):395-401). Adiabatic pulses that invert more than two bands have been used for Hadamard-encoded localized spectroscopy (Goelman G. Hadamard encoding with surface coils for high SNR MR spectroscopy. Magn Reson Imaging 1999; 17(5): 777-781), and cardiac tagging. The multiple bands were achieved either by adding pulses after a frequency and time-shift (Goelman G. Fast Hadamard spectroscopic imaging techniques. J Magn Reson B 1994; 104(3):212-218), or by creating a DANTE pulse train. The DANTE pulse train tends to be longer, requiring a great deal of RF power for the excitation of many identical bands. These methods use adiabatic inversion pulses that may work with a non-homogeneous RF excitation coil, but these pulses typically deposit much more RF power in the sample than comparable non-adiabatic pulses. Thus, the use of these pulses can pose a problem when scanning biological samples and especially when scanning human subjects.

An adiabatic pulse can also be used at lower RF power, but then the effective flip angle may be no less $B_1$-dependent than the flip angle of non-adiabatic pulses. This apparent loss of $B_1$-independence may limit the usefulness of adiabatic pulses as $B_1$-independent selective suppression pulses.

Therefore, there is a need in the art for improved adiabatic pulses for use with selective suppression of unwanted signals from more than one spectral locations in MRI or MRS applications.

SUMMARY

Some embodiments of the current invention provide a magnetic resonance imaging (MRI) system, comprising: a magnetic resonance imaging scanner comprising: a main magnet providing a substantially uniform main magnetic field $B_0$ for a subject under observation; and a radio frequency (RF) coil configured to irradiate a radio frequency (RF) pulse into a region of interest of the subject under observation, wherein the RF pulse comprises a base pulse comprising an adiabatic pulse having a first bandwidth time product (BWTP), wherein the RF pulse selectively suppresses magnetic resonance signals from more than one chemical component or more than one spatial region within the region of interest of the subject under observation, and wherein the adiabatic pulse is characterized by an amplitude modulation function and a frequency modulation function.

Some embodiments of the current invention provide a method to obtain a radio frequency (RF) pulse to be transmitted by a RF coil into a region of interest of a subject under observation in a magnetic resonance scanner having a main magnet, the method comprising: receiving parameters relating to magnetic resonance spectral locations corresponding to more than one chemical component or more than one spatial region within said region of interest; choosing at least one adiabatic pulse to form a base pulse in said RF pulse whose frequency response has notches at said spectral locations; and transmitting said RF pulse to selectively suppress magnetic resonance signals from said magnetic resonance spectral locations corresponding to said more than one chemical component or said more than one spatial region within said region of interest.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
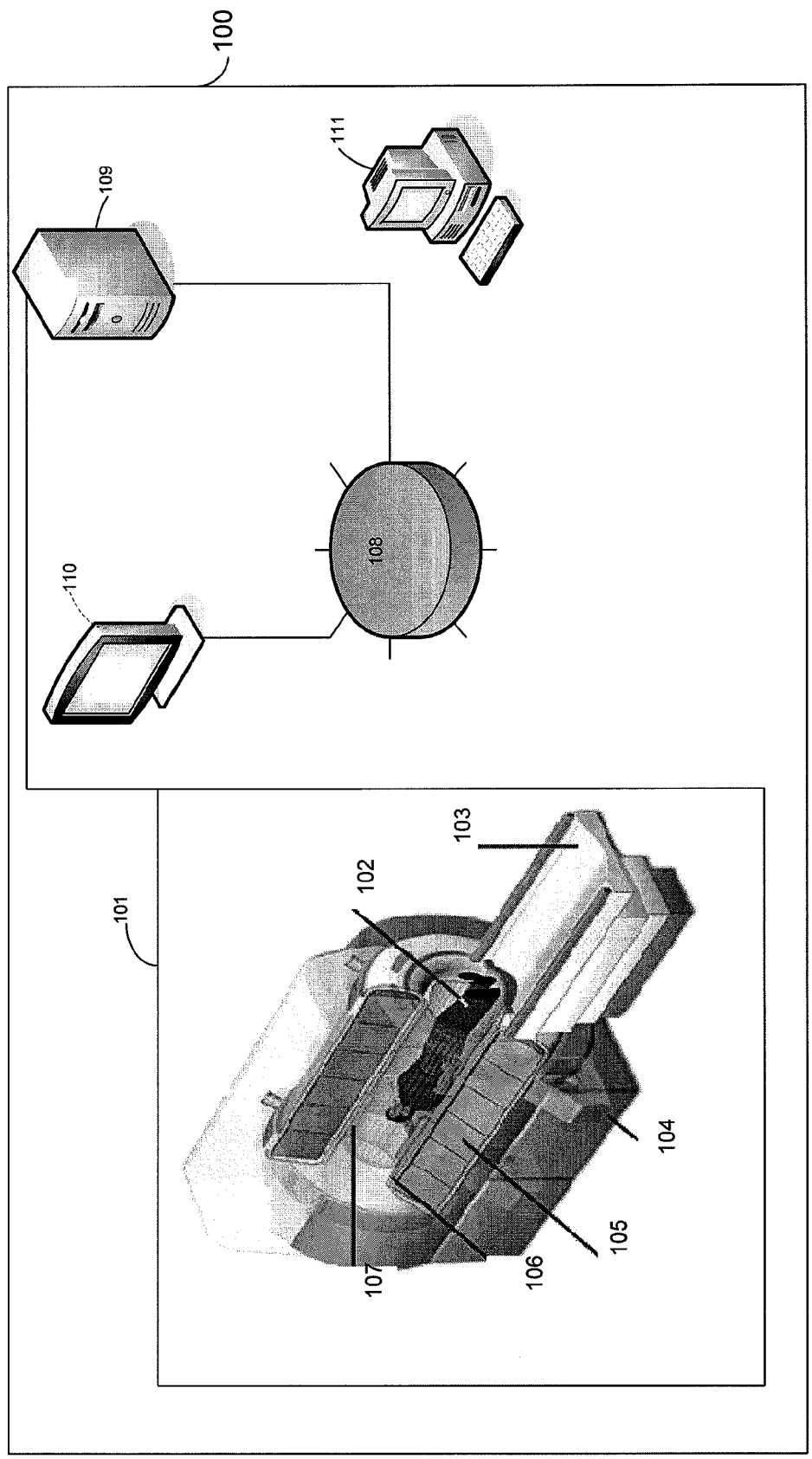
FIG. 1 is a schematic illustration of a magnetic resonance imaging (MRI) system according to an embodiment of the current invention.

FIG. 1 is a schematic illustration of a magnetic resonance imaging (MRI) system 100 according to an embodiment of the current invention.

The MRI system 100 includes a magnetic resonance scanner 101, a data storage unit 108, and a signal processing unit 109. Magnetic resonance scanner 101 has a main magnet 105 providing a substantially uniform main magnetic field $B_0$ for a subject 102 under observation on scanner bed 103, a gradient system 106 providing a perturbation of the main magnetic field $B_0$ to encode spatial information of the constituent water molecules with a region of interest of subject 102 under observation, and a radio-frequency (RF) coil system 107 to transmit electromagnetic waves and to receive magnetic resonance signals from subject 102.

RF coil system 107 comprises at least one radio frequency (RF) coil configured to irradiate a radio frequency (RF) pulse into a region of interest of said subject under observation. The RF coil may be, for example, a surface coil, a neck coil, an extremity coil, a head coil, a body, a phased-array coil, etc. The RF coil may be embodied as a solenoid, a planar, a volume, a quadrature coil, or variations thereof. The RF coil may be for transmission only or for both transmission and reception. RF coil system 107 may further comprise a power amplifier to amplify the RF pulse being transmitted or the received magnetic resonance signals. The power amplifier may be programmed or configured to amplify at more than one level of amplification. RF coil system 107 may further comprise matching and/or tuning networks for impedance matching and/or frequency tuning purposes.

The RF pulse being transmitted by the RF coil may comprise a base pulse comprising an adiabatic pulse with a corresponding bandwidth time product (BWTP). The adiabatic pulse can be described with an amplitude modulation function and a frequency modulation function. As will be discussed below, the adiabatic pulse may be a form of a hyperbolic-secant (HS) pulse; the base pulse may further comprise a blunt pulse whose BWTP is substantially smaller than that of the adiabatic pulse to form a hyper-pulse; and the RF pulse may further comprise a time-reversed instance of the hyper-pulse. The RF pulse may also comprise at least a new instance of the base pulse with a new scaling factor for the amplitude modulation or the frequency modulation. The RF pulse may be transmitted immediately preceding a read-out gradient pulse. The RF pulse may selectively suppress magnetic resonance signals from more than one chemical components or more than one spatial regions within the region of interest of said subject under observation. The chemical components may comprise at least one of: water, triacylglycerol, and N-acetyleaspartase (NAA). The RF pulse may be applied in association with spoiler gradients to dephase the MR signals from the more than one chemical components or the more than one spatial regions within the region of interest. The RF pulse may be applied in association with inversion delays to attenuate the MR signals from the more than one chemical components or the more than one spatial regions within the region of interest. Inversion delays may be generated by timing circuits in magnetic resonance imaging scanner 101. Example timing circuits may include, but are not limited to, a circuit board with hardware components (e.g., resistors, transistors, capacitors, inductors, etc.), or a programmable device (e.g., field programmable gated array, digital signal processing unit, etc). The RF pulse may be applied to selectively refocus the MR signals from the more than one chemical components or the more than one spatial regions with the region of interest. The RF pulse may further suppress outer volume signals.

Data storage unit 108 is in communication with signal processing unit 109 to store magnetic signals from the region of interest of subject 102 under observation. The subject may be, for example, a human, an animal, a phantom, a sample, or combinations thereof. The region of interest may be, for example, a brain, a heart, a muscle, a liver, a knee, a neck, etc.

Data storage unit 108 may be, for example, a hard disk drive, a network area storage (NAS) device, a redundant array of independent disks (RAID), a flash drive, an optical disk, a magnetic tape, a magneto-optical disk, etc. However, the data storage unit 108 is not limited to these particular examples. It can include other existing or future developed data storage devices without departing from the scope of the current invention.

Signal processing unit 109 is in communication with magnetic resonance scanner 101 to receive magnetic resonance signals from the region of interest in response to the RF pulse. Signal processing unit 109 may be partially or totally incorporated within a structure housing magnetic resonance scanner 101. Signal processing unit 109 may be at least partially incorporated in a workstation that is structurally separate from and in communication with magnetic resonance scanner 101. Signal processing unit 109 may be incorporated in a workstation that is structurally separate from and in communication with magnetic resonance scanner 101. A workstation can be a computer having at least one central processing unit (CPU) and one memory, for example, static random access memory (SRAM), dynamic random access memory (DRAM), erasable programmable random access memory (EPROM), non-volatile Flash memory, etc.

Signal processing unit 109 may perform spectral editing for the received magnetic resonance signals. The processed results may be visualized on a display device, such as, for example, viewing station 110 or a console station 111. Viewing station 110 or console station 111 may be, for example, a cathode ray tube (CRT) monitor, a liquid crystal display (LCD) monitor, a digital light projection (DLP) monitor, a plasma screen, an organic light emitting diode (OLED), etc. The processed results may be used for further analysis and diagnosis.

Figure 2:
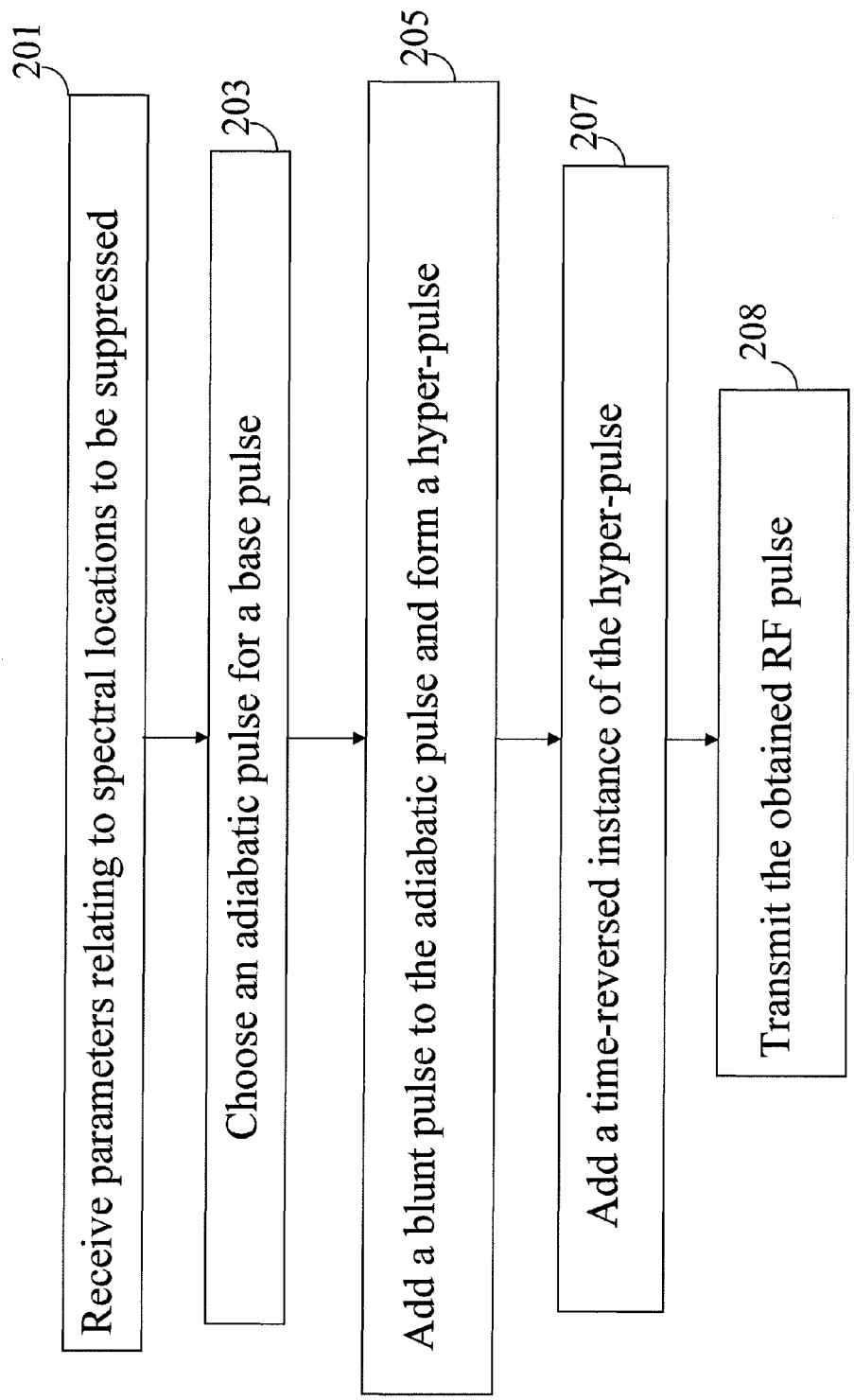
FIG. 2 shows a flow chart according to some embodiments of the current invention.

FIG. 2 shows a flow chart according to some embodiments of the current invention. The flow chart corresponds to a method to obtain a radio frequency (RF) pulse to be transmitted by a RF coil into a region of interest of a subject under observation in a magnetic resonance scanner having a main magnet. Box 201 is to receive parameters relating to magnetic resonance spectral locations corresponding to more than one chemical component or more than one spatial region within the region of interest. The chemical component can be, for example. water, triacylglycerol, and N-acetyleaspartase (NAA). However, the invention is not limited to only these examples. The parameters may be received from a user input. For example, a user may specify the frequency shifts of unwanted chemical components such as fat and water. The parameters may also come from data storage unit 108. Box 203 is to choose at least one adiabatic pulse to form a base pulse in said RF pulse whose frequency response has notches at the intended spectral locations. The notches are spectrally asymmetric such that one edge of the transition band in the frequency response profile is substantially sharper than the other. This asymmetry may achieve adequate signal suppression within the stop-band while reducing total SAR compared to adiabatic RF pulses with symmetric edges of the transition band, as will be discussed. The notches can have identical spectral widths in some embodiments. The notches may even have non-identical spectral widths such that the stop-band widths at the intended spectral locations are different. The base pulse is a logic component making up the RF pulse being designed. The adiabatic pulse may be a form of a hyperbolic-secant (HS) pulse. The adiabatic pulse may be highly selective. Example highly selective HS pulses ($HS_N$) may have an order of less than 1. Box 205 is to add a blunt pulse to the adiabatic pulse in the base pulse to generate a hyper-pulse. The blunt pulse is non or weakly selective. An example blunt pulse may be a Numerically-Optimized-Modulation (NOM) pulse. Another example may be a HS pulse ($HS_N$) with an order of at least 2. Box 207 is to add to the RF pulse a time-reversed instance of the hyper-pulse. The added instance may be scaled differently than the first instance. Box 208 is to transmit the obtained RF pulse to selectively suppress magnetic resonance signals from the magnetic resonance spectral locations corresponding to the more than one chemical component or the more than one spatial region within the region of interest.

For a given selective pulse, the transition bandwidth relative to the actual excitation or inversion bandwidth (BW) is inversely proportional to the product of pulse time ($T_p$) and BW. Trade-off between pulse length and frequency band definition has to be optimized for each MR application. By sharply defining just one side of the suppression band, less RF pulse time is spent on defining an edge that often servers no real function. This can be achieved by combining sharply defined adiabatic pulses with non- or weakly-selective (blunt) pulses into hyper-pulses (Hwang T L, van Zijl P C M, Garwood M. Asymmetric adiabatic pulses for NH selection. Journal of Magnetic Resonance 1999; 138(1):173-177). The sharp pulses are typically high-quality hyperbolic-secant (HS) pulses (Silver M S, Joseph R I, Hoult D I. Selective Spin Inversion in Nuclear Magnetic-Resonance and Coherent Optics through an Exact Solution of the Bloch-Riccati Equation. Phys Rev A 1985; 31(4):2753-2755), or derivatives of the HS pulse, $HS_N$ pulses, where the sech amplitude modulation function is modified to AM(0=sech(β tn), where β is a constant determining pulse truncation levels (Tannus A, Garwood M. Improved performance of frequency-swept pulses using offset-independent adiabaticity. J Magn Reson Ser A 1996; 120(1):133-137). These pulses can have very sharp profiles when n<1. When combining sharp pulses with an essentially non-selective Numerically-Optimized-Modulation (NOM) pulse (Ugurbil K, Garwood M, Rath A R. Optimization of Modulation Functions to Improve Insensitivity of Adiabatic Pulses to Variations in $B_1$ Magnitude. Journal of Magnetic Resonance 1988; 80(3):448-469), or a higher order HS pulse ($HS_N$, with n>2), the resulting hyper-pulses have a highly asymmetric amplitude and frequency modulation waveform. These pulses can have sharp edge definition only on one side of the inversion band with pulse durations that are significantly reduced compared to similarly sharp symmetric pulses, resulting in reduced sequence lengths and total deposited RF power.

Simultaneous RF transmission of multiple pulses rather than sequential excitation of multiple bands could also be used to reduce sequence lengths, but scanners are usually not equipped with multiple independent excitation channels. Fortunately, simultaneous multi-band excitations can be achieved with a single output, using RF waveforms obtained by addition of RF pulses (Patt S L. Single- and Multiple-Frequency-Shifted Laminar Pulses. Journal of Magnetic Resonance 1992; 96:94-102, Ouwerkerk R, Edden R A. Multi-Band Adiabatic Pulses. 2006 March; Seattle, Wash., USA. p 3006). Although summing phase shifted amplitude pulses to achieve multi-band excitation is an established method, problems arise when excitation bands are close together (Kupce E, Freeman R. Close Encounters between Soft Pulses. Journal of Magnetic Resonance Series A 1995; 112(2):261-264, Steffen M, Vandersypen L M K, Chuang I L. Simultaneous soft pulses applied at nearby frequencies. Journal of Magnetic Resonance 2000; 146(2):369-374). If only a few bands are required, the method of adding pulses as described by Goelman (Goelman G. Fast Hadamard spectroscopic imaging techniques. J Magn Reson B 1994; 104(3): 212-218) may be preferable. This method may substantially reduce the $B_1$ range over which the pulses behave like singleband adiabatic pulses, but many MR applications do not require $B_1$ field insensitivity over a very large range. Moreover, for saturation sequences, the adiabatic pulses can also be used with $B_1$ fields under the adiabatic threshold where these pulses are non-adiabatic, as will be discussed later in association with FIG. 8.

A base pulse in the designed RF pulse can be asymmetrical, with unequal bandwidths, or unequal amplitude. Time-reversing a new instance of the base pulse and adding the time-reversed instance can produce dual-band inversion pulses with a very sharp pass-band according to an embodiment of the current invention. The use of hyper-pulses, with a time-reversed and frequency-shifted copy, may yield adiabatic band-pass pulses that are suitable for outer volume suppression in MRS or dual-slab inversion in perfusion measurements. For dual-band pulses with individual inversion bandwidths, $BW_i$, the frequency shifts, $\Delta f$, should be related to BW and pass-band width (PBW). Typically $\Delta f_i = \pm(PBW+BW_i)/2$, although fine-tuning may be required to achieve the exact desired profiles.

Adding identical pulses as amplitude-phase vectors after a linear phase shift will result in interference patterns, creating pulses with many discontinuities in amplitude and frequency modulations and bad performance. In one of Goelman's methods two identical $HS_1$ pulses are added after a time shift which reduces the interference patterns (Goelman G. Two methods for peak RF power minimization of multiple inversion-band pulses. Magn Reson Med 1997; 37(5):658-665). The inventors found that the added pulses do not have to be identical and adding non-identical pulses sometimes obviates the need for the time shift. Scaling-created inequality may obviate the need for the time shift. With no time shift, two identical pulses can be added with different scaling factors on the amplitude and/or frequency modulation function to create a dual-band pulse with two different BWs and different relations between $B_1$ and flip-angle.

Figure 3:
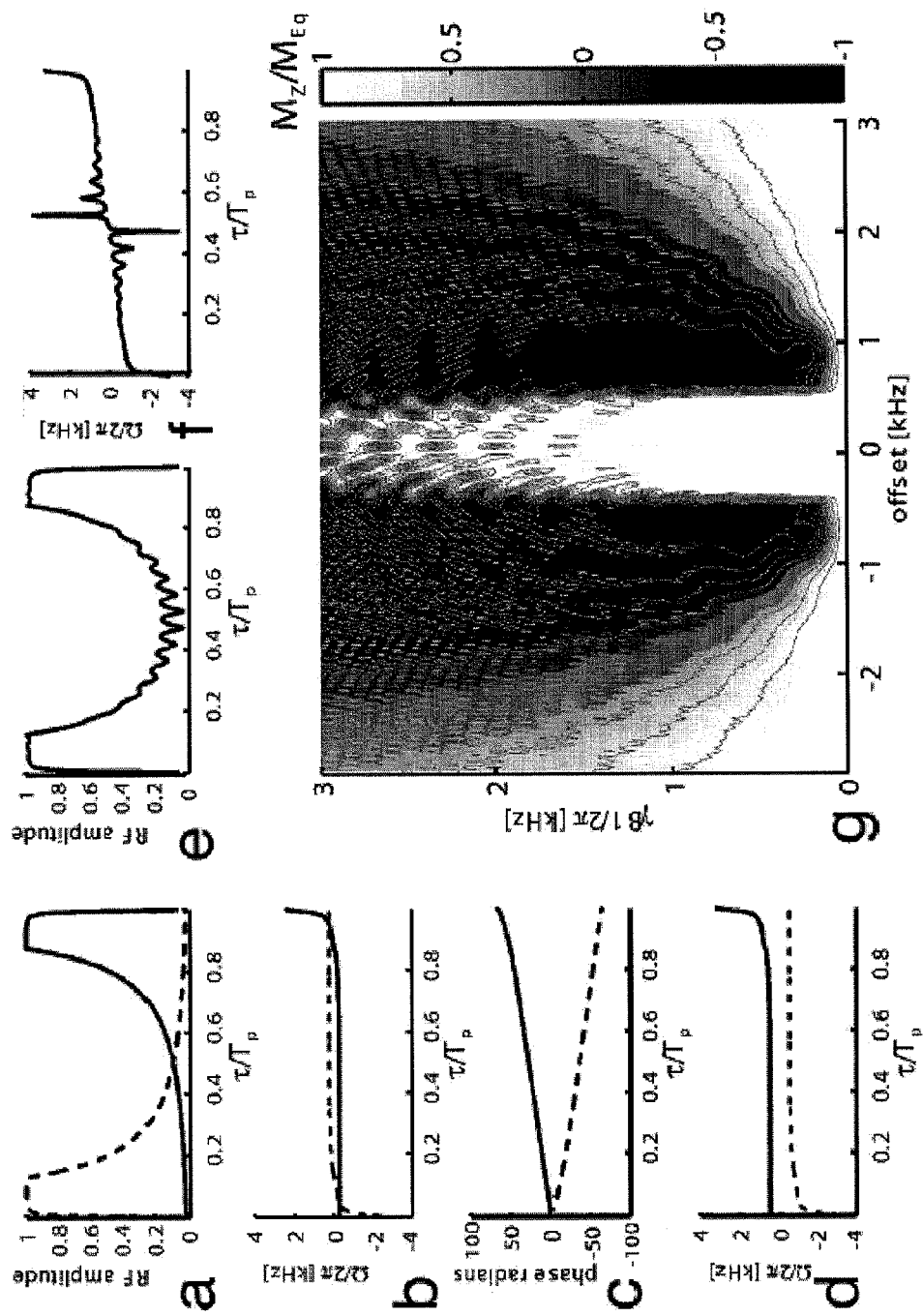
FIG. 3 illustrates a RF pulse designed according to some embodiments of the current invention and its simulated frequency response.

FIG. 3 illustrates an RF pulse designed according to some embodiments of the current invention and its simulated frequency response. The RF pulse is a dual-band pulse (or non-selective inversion pulse with a sharp central pass-band) created from a hyper-pulse. The hyper-pulse, created by combining half of a non-selective NOM inversion pulse (compressed to ⅛ of the duration of the final pulse) and half of a highly selective $HS_{0.75}$ pulse (stretched to ⅞ of the final pulse length). In (a), amplitude modulations are shown for forward (solid lines) and time-reversed copy (dashed lines) as a function of time τ normalized to pulse duration $T_p$. In (b), the corresponding frequency modulations are shown in kHz for $T_p=18$ ms. In (c), the corresponding phase modulations after the addition of linear phase ramps are shown. In (d), the corresponding frequency modulations after the frequency shift effected by the phase ramps are shown. In (e) and (f), amplitude and frequency modulations are shown (obtained by numerical differentiation of the phase modulation). In (g), simulated responses ($M_z/M_{Eq}$) are shown as a function of peak $B_1$ field and offset frequency for this pulse at $T_p=18$ ms, ignoring relaxation effects during the pulse.

Figure 4:
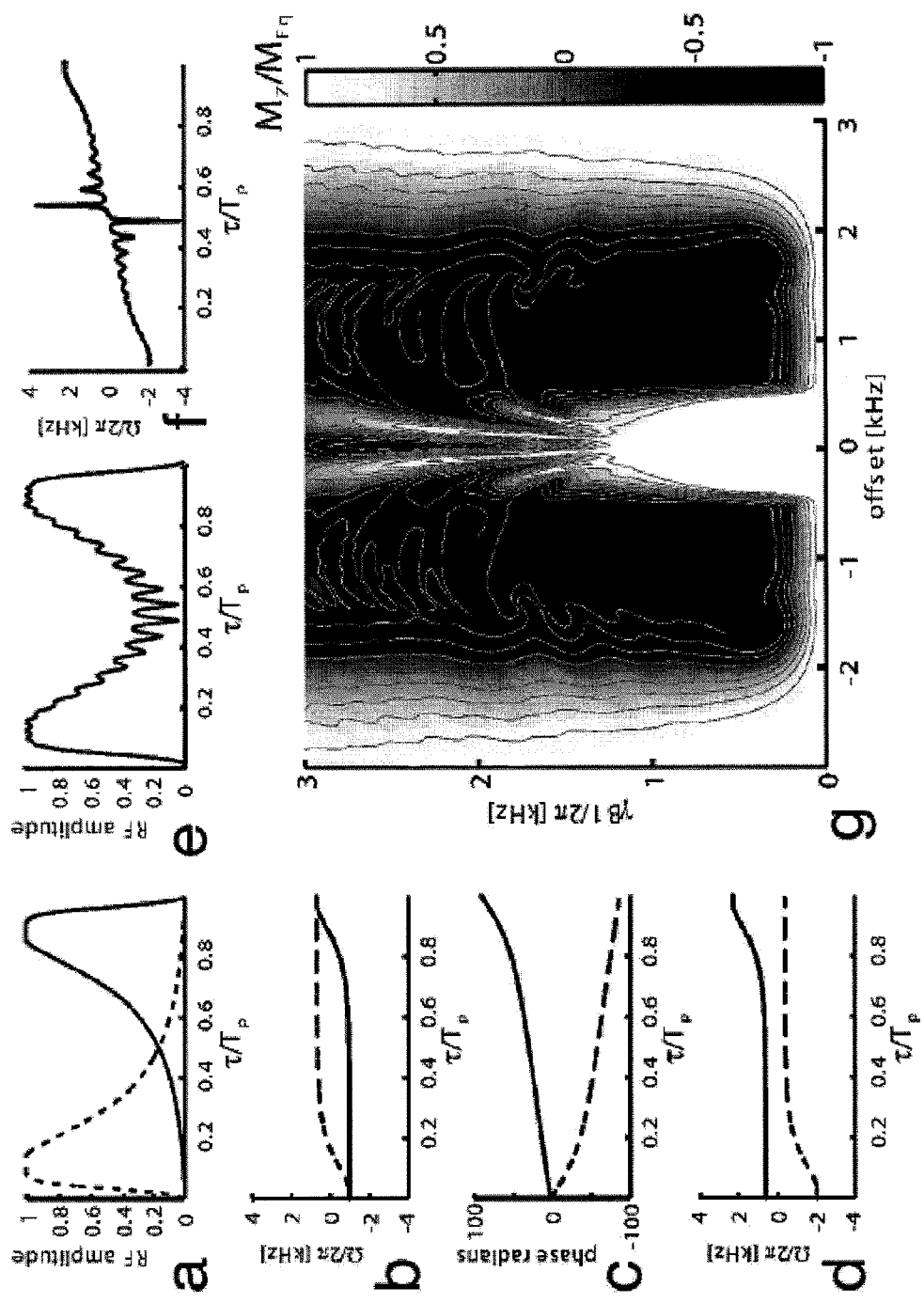
FIG. 4 illustrates another RF pulse designed according to some embodiments of the current invention and its simulated frequency response.

FIG. 4 illustrates another RF pulse designed according to some embodiments of the current invention and its simulated frequency response. The base pulse is a hyper-pulse created from an $HS_{4.5}$ pulse (blunt, ⅛th of the pulse time) and a selective $HS_{0.75}$ pulse (sharp, ⅞th of the pulse time). In (a), the amplitude modulations are shown for the forward (solid line) and time reversed (dashed line) copies as a function of normalized pulse time $\tau/T_p$. In (b), the corresponding frequency modulations are shown in kHz for $T_p=18$ ms. In (c), phase modulations are shown with phase ramps. In (d), resulting frequency-shifted modulations are shown. In (e) and (f), the resulting amplitude and frequency modulations are shown. In (g), the simulated responses ($M_z/M_{Eq}$) are shown as a function of peak $B_1$ field and offset frequency for this pulse at $T_p=18$ ms, ignoring relaxation effects during the pulse.

For the non-selective pulse halves, a NOM adiabatic half-passage pulse was used, calculated from a sin/cos modulated adiabatic half passage (AHP) pulse and optimized for υ=0.1 to 5 (υ being an RF scaling factor applied to the RF amplitude), using Eq. [10] in the reference (Ugurbil K, Garwood M, Rath A R. Optimization of Modulation Functions to Improve Insensitivity of Adiabatic Pulses to Variations in B1 Magnitude. Journal of Magnetic Resonance 1988; 80(3):448-469.). The resulting pulse inverts a wide band, which increases roughly proportionally with $B_1$, cut through by a sharp pass-band of width (PBW) that is invariant with $B_1$ up to γ B1/2π≈PBW, as shown in (g) of FIG. 3. Alternatively, the first half of a sharp $HS_{3/4}$ pulse was combined with the (blunt) second half of an HSN pulse with N>2, typically 4.5. This yields pulses that have two inversion bands of more or less constant width flanking a sharp pass-band, as shown in (g) of FIG. 4.

Figure 5:
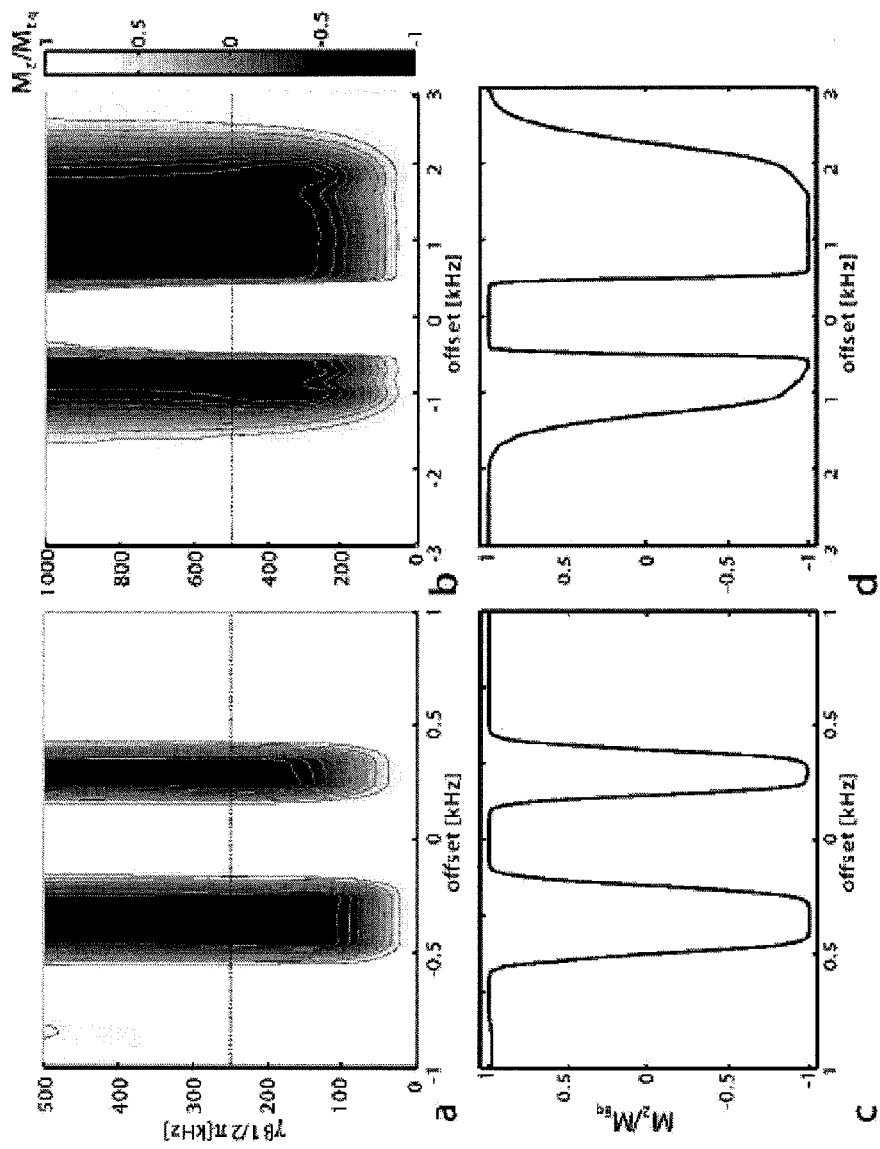
FIG. 5 shows two more RF pulses and the corresponding simulated frequency responses according to some embodiments of the current invention.

FIG. 5 shows two more RF pulses that invert dual bands with differing inversion band parameters according to some embodiments of the current invention and the corresponding simulated frequency responses. Inversion pulse responses are plotted as a function of offset frequency and peak $B_1$ field of two types of dual-band adiabatic hyper pulses, each with unequal inversion bands. In (a), the frequency response is shown for a 40 ms RF pulse constructed as the sum of two HS pulses, with bandwidths of 300 and 200 Hz and the amplitude of the 300 Hz BW pulse multiplied by 2 before addition. In (b), the frequency response is shown for a 25 ms RF pulse constructed as the sum of two hyper-pulses. Each hyper-pulse is created from the sum of an $HS_{4.5}$ pulse (blunt) and a selective $HS_{0.75}$ pulse (sharp), with bandwidths (BWs) of approximately 0.75 and 15 kHz, respectively. The amplitude of the $HS_{0.75}$ pulse is scaled by a factor of 2.25 before summation. In (c), the response is shown for the RF peak amplitude indicated in (a) by the dotted line ($\gamma B1/2\pi=250$ Hz). In (d), the response is shown for the RF peak amplitude indicated in (b) by the dotted line ($\gamma B1/2\pi=500$ Hz).

Dual HSN pulses with two asymmetric bands may be created from two HSN pulses with the power 'n' varied between 1.5 and 3.5 in order to keep the total pulse length at 30 ms or less for a pass-band of 400 Hz. For simultaneous water/fat suppression with these pulses, the widths of the individual bands may be adjusted in accordance with the difference in peak widths of water and fat in in-vivo MR spectra. Two examples of dual-band pulses where the bandwidths are non-identical are shown in FIG. 5.

All computations were performed in Matlab (Mathworks, Natick, Mass.) on an Apple G5 computer. Band-pass inversion pulses were constructed from various types of hyper-pulses (Hwang T L, van Zijl P C M, Garwood M. Asymmetric adiabatic pulses for NH selection. Journal of Magnetic Resonance 1999; 138(1):173-177). The hyper-pulses are constructed from pulses with large $BW$-$T_p$ product (BWTP) having inversion bands with sharp edges, and either essentially non-selective inversion pulses (FIG. 3) or selective pulses with low BWTP (FIGS. 4 and 5).

Figure 6:
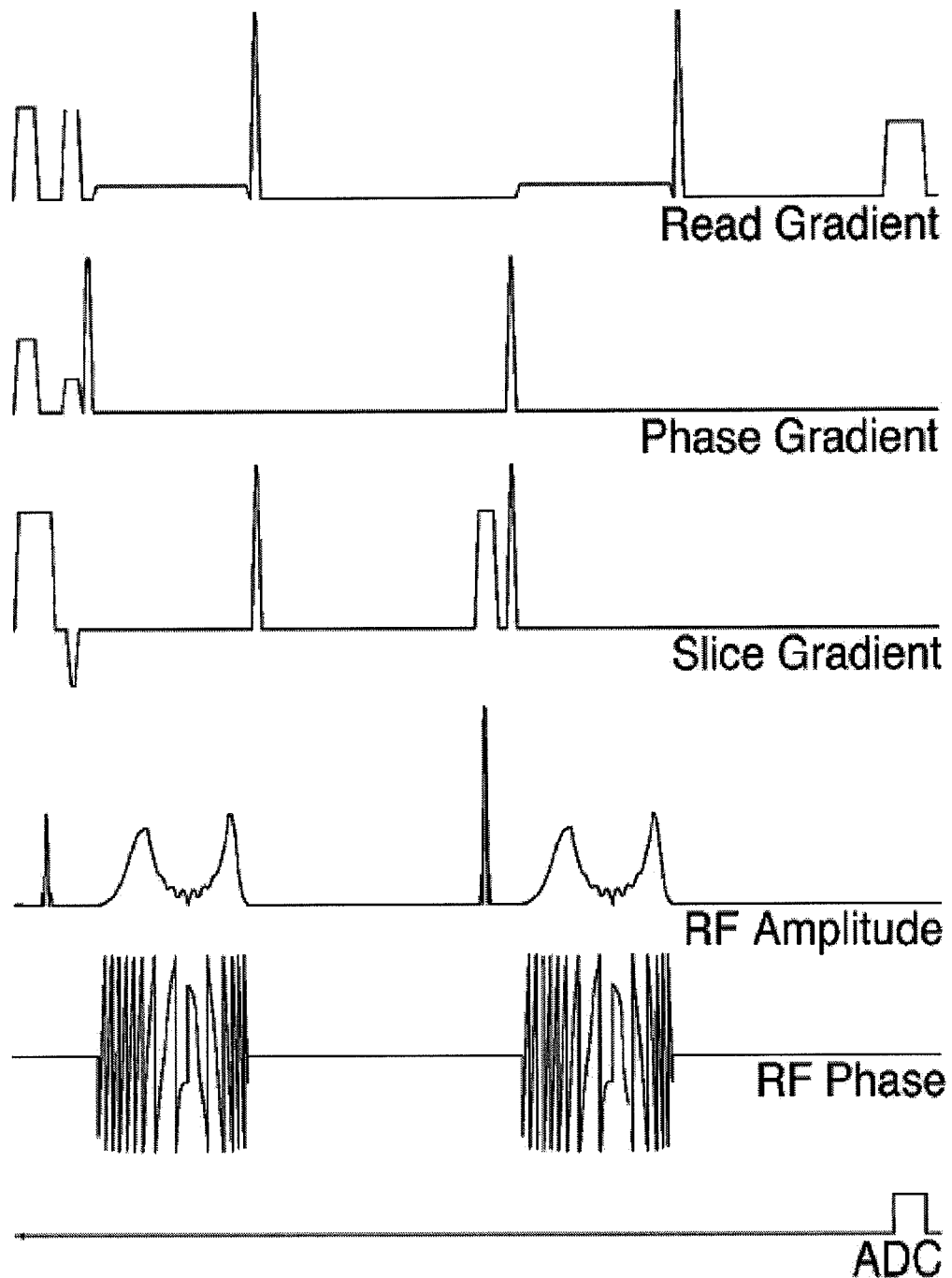
FIG. 6 shows the timing diagram of a magnetic resonance imaging pulse sequence using a RF pulse designed according to some embodiments of the current invention.

FIG. 6 shows the timing diagram of a magnetic resonance pulse sequence using an RF pulse designed according to some embodiments of the current invention. The pulse sequence is for measuring the MEGA suppression profile of a dual-band adiabatic pulse. The sequence comprises a spoiler pulse on all gradients, followed by a slice-selective 90° pulse with a refocusing gradient, the first MEGA chemically selective RF pulses and associated MEGA gradient pulses, a 180° slice-selective refocusing pulse, the second MEGA RF and MEGA gradient pulses, and finally, the readout gradient and data acquisition.

The use of dual-band pulses in a MEGA suppression scheme was tested with phantom experiments on a 1.5 T MR scanner (Magnetom-Avanto, Siemens Medical Solutions Erlangen, Germany) using a phased-array receive head coil and body coil excitation. The test pulse sequence, as shown in FIG. 6, was a spin echo (SE) imaging sequence, modified by insertion of a pair of 31 ms dual-band adiabatic selective refocusing pulses preceded and followed by matched crusher gradients. The sequence was run with TR/TE=500/100 ms, a 5 mm slice thickness, and a 25 cm FOV on a 2 L bottle with $NiCl_2$ doped water with a $T_1$ of about 0.25 s. After shimming and optimization of the SE 90° and 180° pulses, several images were recorded with the RF amplitude of the selective refocusing pulse pair varied between 0 and 9 µT. During the dual-band adiabatic pulses, a gradient was applied in the readout direction with amplitude adjusted to 20 mm/Hz to create a 2 cm pass-band in the images. The pulse tested in this sequence was designed to have a 200 Hz PBW at $T_p=31$ ms. The width of the high and low frequency suppression bands was 250 and 350 Hz, respectively. The base pulses used for this dual-band RF pulse were hyper-pulses created from $HS_{3/4}$ (sharp) and $HS_4$ (blunt) pulses.

Figure 7:
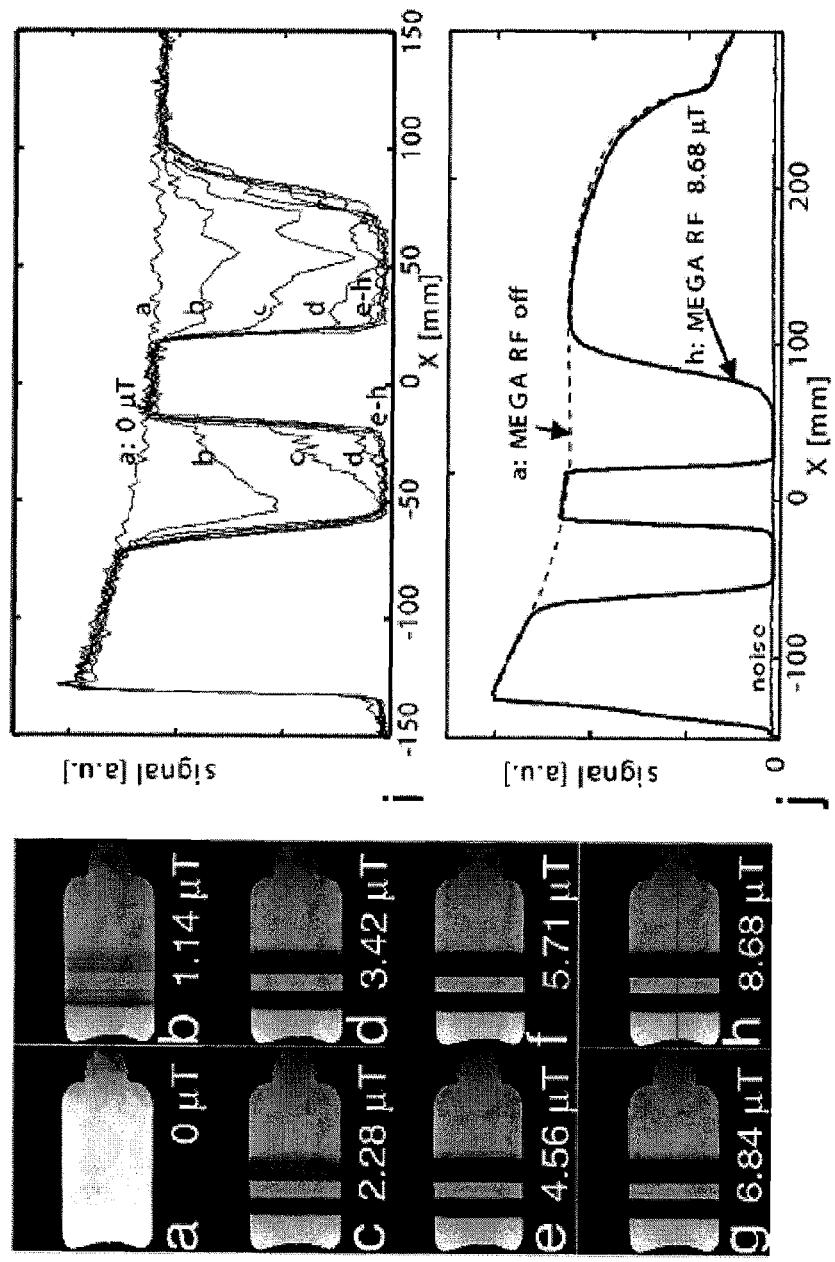
FIG. 7 shows results from a phantom using the pulse sequence shown in FIG. 6.

FIG. 7 shows results from a phantom using the pulse sequence shown in FIG. 6. In (a-h), SE images are displayed for a bottle using the sequence shown in FIG. 6, with MEGA RF pulse amplitudes set to the values shown. In (i), profiles through the horizontal mid-line of the images (a-h) are shown. The position of this profile is indicated by a horizontal line in (h). In (j), averaged signals with and without suppression are shown. The solid black line correspond to the mean signal of 110 image lines over the width of the bottle image. Clearly, at RF amplitudes of 4.56 µT and beyond, excellent selective signal suppression is obtained. In (j), profiles are shown for the SE images in (h), with a MEGA RF of 8.68 µT. The thin dotted line in (j) corresponds to the mean signal over the width of the bottle image in (a), with MEGA RF pulse off. The thin gray solid line labeled as "noise" indicates the average noise level in the top 70 lines of the images in (a) and (h) that are outside the bottle. The profile result from (h) demonstrates a very sharp profile of the pass-band, with excellent suppression of signals on either side. Thus, application of a dual-band pulse in a MEGA pulse sequence proved that dual-band suppression is possible with the pulses working as adiabatic inversion pulses.

There are several ways to use adiabatic pulses for signal suppression. In true adiabatic mode (RF powers above the adiabaticity threshold), adiabatic pulses can be used to selectively invert signals. In combination with the right inversion delay, good signal suppression can be achieved. This technique requires either a good a priori estimate of the $T_1$ of the signal, or an optimization of inversion delays before each experiment. In addition, a pair of pulses can be used after the excitation pulse in a selective refocusing sequence. With this method, excellent $T_1$-independent signal suppression is possible. With non-adiabatic pulses, the MEGA selective refocusing sequence (Mescher M, Merkle H, Kirsch J, Garwood M, Gruetter R. Simultaneous in vivo spectral editing and water suppression. NMR in Biomedicine 1998; 11(6):266-272) has been used for solvent signal suppression as well as spectral editing (Terpstra M, Gruetter R. 1H NMR detection of vitamin C in human brain in vivo. Magn Reson Med 2004; 51(2):225-229, Edden R A, Barker PB. Spatial effects in the detection of gamma-aminobutyric acid: Improved sensitivity at high fields using inner volume saturation. Magn Reson Med 2007; 58(6):1276-1282). The MEGA sequence can also be used with selective adiabatic pulses to achieve $B_1$-insensitive signal suppression (Ouwerkerk R. Dual-Band Adiabatic Selective Refocussing for Signal Suppression in High Field MR. Proc 15th Meeting ISMRM; 2007 May; Berlin, Germany. P 1678).

The MEGA pulse scheme is applicable only in spin-echo-based sequences and the minimum achievable echo time might be too long for some applications. When shorter echo-times are desired, selective signal suppression can only be achieved with sequences that precede the excitation pulses. When used with RF powers below the adiabaticity threshold, adiabatic pulses could be used to replace conventional selective excitation pulses immediately preceding the acquisition sequence. As such, the response will be less critically $T_1$-dependent. Although in that regime the flip angle is $B_1$-dependent, excitation profiles of adiabatic pulses at lower flip angles may have some desirable properties. In contrast to pulses without frequency modulations, the frequency excitation profiles of adiabatic pulses at lower flip angles hardly change with effective flip angle, whereas non-adiabatic pulses yield the desired profiles only around a specific design flip angle, necessitating different pulses for optimal excitation, inversion, or refocusing. $B_1$-insensitive water suppression (Ws) can be achieved with conventional pulses over a (limited) range of $B_1$ values with the WET (Ogg R J, Kingsley P B, Taylor J S. Wet, a T-1-Insensitive and B-1-Insensitive Water-Suppression Method for in-Vivo Localized H-1-NMR Spectroscopy. Journal of Magnetic Resonance Series B 1994; 104(1):1-10.) and VAPOR (Tkac I, Starcuk Z, Choi I Y, Gruetter R. In vivo 1H NMR spectroscopy of rat brain at 1 ms echo time. Magn Reson Med 1999; 41(4):649-656) comprising repetitions of selective excitations followed by crushers. The pulse amplitudes and repetitions intervals can be optimized to achieve signal suppression over a predetermined range of $B_1$ and/or $T_1$ values. Rather than replacing selective pulses by adiabatic pulses in these optimized sequences, a new optimization scheme can be used to account for the non-sinusoidal relation between $B_1$ and flip angle that is typical for adiabatic pulses, as discussed below.

Figure 8:
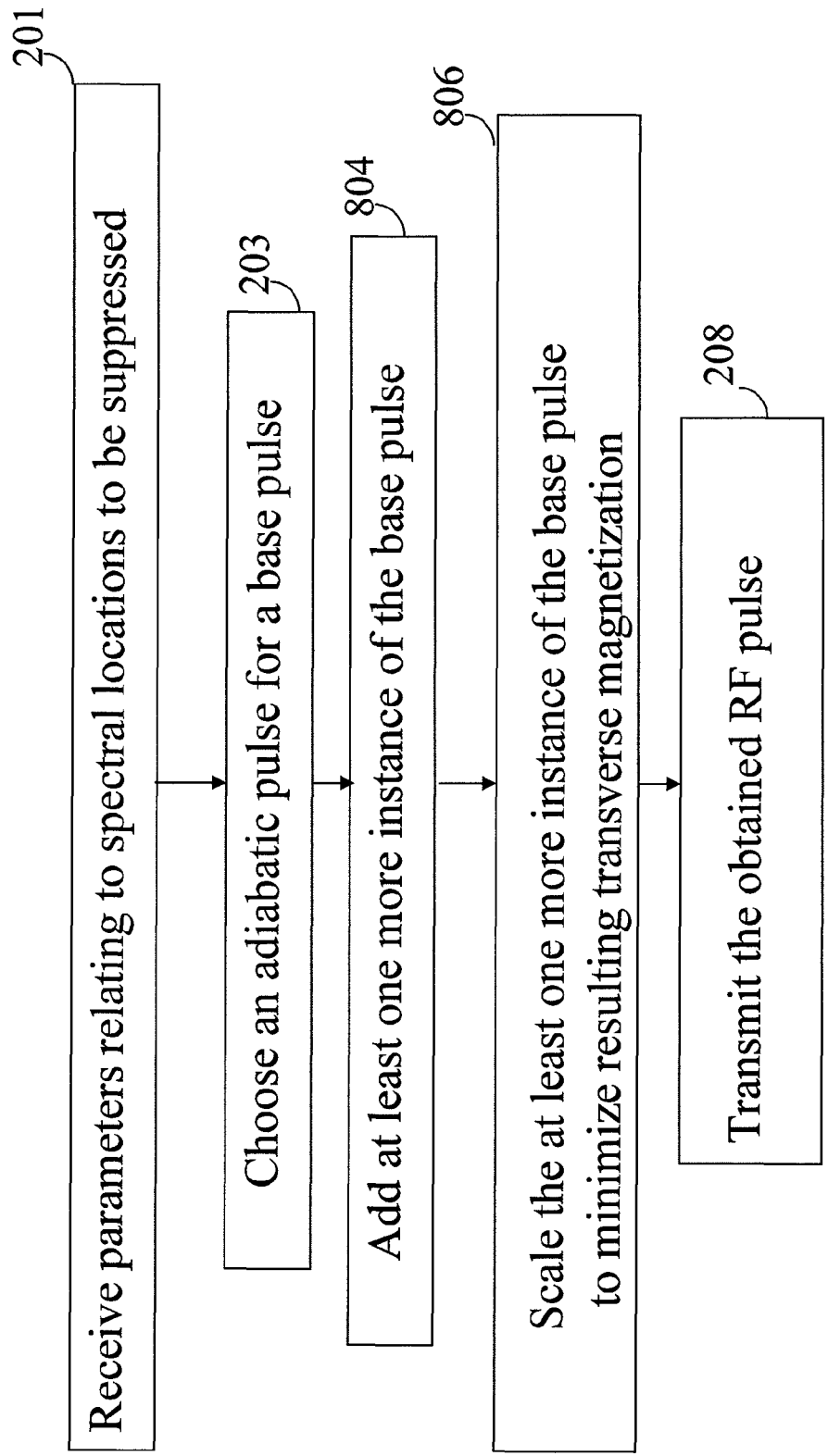
FIG. 8 shows another flow chart according to some embodiments of the current invention.

FIG. 8 shows another flow chart according to some embodiments of the current invention. Box 201 is to receive parameters relating to magnetic resonance spectral locations corresponding to more than one chemical component or more than one spatial region within the region of interest. Box 203 is to choose at least one adiabatic pulse to form a base pulse in said RF pulse whose frequency response has notches at the intended spectral locations. Box 804 is to add at least one new instance of the base pulse with a new scaling factor for the amplitude modulation function or the frequency modulation function. Box 806 is to minimize residual transverse magnetization corresponding to the more than one chemical components or the more than one spatial regions within the region of interest of the subject under observation. The minimization takes into account of spatial $B_1$ variations over the region of interest and $T_1$ relaxation effect when the RF pulse is being transmitted to the region of interest. Box 208 is to transmit the obtained RF pulse to selectively suppress magnetic resonance signals from the magnetic resonance spectral locations corresponding to the more than one chemical component or the more than one spatial region within the region of interest.

For applications that require only a limited insensitivity to $B_1$ inhomogeneity, solutions with fewer pulses may be found by optimizing the $B_1$-insensitive response over limited ranges of $B_1$ field strengths with fewer pulses.

Fast optimization depends on the speed of calculating the response of an adiabatic pulse. A numerical approach using the Bloch equations is not suitable for this purpose because this requires calculation of the response per pulse point. An analytical expression for the response after the whole pulse is much faster. For an adiabatic $HS_1$ pulse, the analytical expression for the on-resonance $M_z/M_{Eq}$ can be derived from Eq. 17 in Silver, M S et al. (Silver M S, Joseph R I, Hoult D I. Selective Spin Inversion in Nuclear Magnetic-Resonance and Coherent Optics through an Exact Solution of the Bloch-Riccati Equation. Phys Rev A 1985; 31(4):2753-2755) by setting the off-resonance to zero (see Appendix A):

$$\frac{M_z}{M_{Eq}}(B_1) = \frac{1 - \cosh(\pi \cdot \mu) + 2 \cdot \cos\left[\pi \cdot \mu \sqrt{\left(\frac{\lambda \cdot B_1}{BW \cdot \pi}\right)^2 - 1}\right]}{1 + \cosh(\pi \cdot \mu)} \quad (1)$$

with $\mu$: quality factor, BW: bandwidth [Hz], with $B_1$: transmit RF filed, $\gamma$: gyromagnetic ratio, and the cosine of complex number z may be expressed as:

$$\cos(z) = \frac{e^{iz} + e^{-iz}}{2} \quad (2)$$

The square-root quantity in the cosine term of the numerator of Eq. 1 is only real for $B_1$ greater than the adiabaticity threshold $B_1$. Below that value, the cosine can still be calculated as the cosine of a complex number using Eq. 2. It has been shown that using this expression, $M_z/M_{Eq}$ can be accurately calculated as a function of $B_1$ (Ouwerkerk R. Fast Sequence Optimization for Superior Signal Suppression with Multiple Hyperbolic Secant Pulses. Proc. 15th Meeting ISMRM; 2007 May; Berlin, Germany. p 1674. (Proc. 15th Meeting ISMRM)) and much faster than numerically with the Bloch equations. Thus, the cumulative effect of a number of sech pulses can be optimized with any stable optimization algorithm. The simulation of $T_1$ recovery between and after pulses is simple to approximate. Realistic modeling of relaxation effects during the RF pulses poses a problem, but the usual approach to this is to calculate longitudinal relaxation over the intervals between pulse centers. Thus, even the inter-pulse delays can be optimized using simulated annealing in a two-dimensional solution space. Using this optimization technique, sequences with multiple adiabatic pulses can be designed for water, fat, or simultaneous water-fat suppression.

TABLE 1

| $B_1$ for | uT | % | | $T_1$ [s] | | | |
|---|---|---|---|---|---|---|---|
| 90° | 0.869 | 100.0 | pulse | 0.5 | 0.75 | 1.00 | 1.50 |
| 3 pulse $B_1$ Min | 0.579 | 66.7 | 1 | 0.8874 | 0.9216 | 0.9058 | 0.8888 |
| $B_1$ Max | 1.159 | 133.3 | 2 | 0.8061 | 0.8557 | 0.8653 | 0.8859 |
| | | | 3 | 1.7115 | 1.6434 | 1.5639 | 1.4805 |
| 5 pulse $B_1$ Min | 0.348 | 40.0 | 1 | 0.6324 | 0.7176 | 0.7786 | 0.7946 |
| $B_1$ Max | 1.391 | 160.0 | 2 | 0.5665 | 0.6689 | 0.7378 | 0.7151 |
| | | | 3 | 1.4143 | 1.4695 | 1.5003 | 1.4389 |
| | | | 4 | 1.1689 | 1.2008 | 1.2157 | 1.1854 |
| | | | 5 | 2.6938 | 2.6005 | 2.5430 | 2.3505 |
| 7 pulse $B_1$ Min | 0.248 | 28.6 | 1 | 0.5309 | 0.5759 | 0.5967 | 0.7151 |
| $B_1$ Max | 1.490 | 171.4 | 2 | 0.7988 | 0.8196 | 0.8355 | 0.8945 |
| | | | 3 | 0.9959 | 1.1003 | 1.1393 | 1.1998 |
| | | | 4 | 0.4314 | 0.5403 | 0.5986 | 0.6815 |
| | | | 5 | 1.9626 | 1.9517 | 1.9456 | 1.9842 |
| | | | 6 | 1.5877 | 1.7095 | 1.7841 | 1.8219 |
| | | | 7 | 3.7123 | 3.5825 | 3.5291 | 3.4493 |

For example, optimal suppression sequences may be obtained with fixed inter-pulse delays according to the above discussion. Table 1 shows optimized coefficients for suppression pulse sequences with minimal fixed inter-pulse delays of 3 ms. The $T_1$ values include 0.5, 0.75, 1, and 1.5 s. Eq. 1 was used in a Levenberg-Marquardt optimization of the cumulative response of the total sequence. Inter-pulse delays between (for crushers) were kept at 3 ms, and $T_1$ weighting was applied for the interval between pulse midpoints. Pulse parameters entered in Eq. 1 were, BW=250 Hz, $\mu$=5, and truncation=1%. This yields an $HS_1$ pulse with a length of 67.5 ms. Inter-pulse intervals were chosen to be 70.5 ms unless they were included in the optimization. The transverse magnetization was set to zero after each pulse to simulate crusher gradients. A two-dimensional simulated annealing algorithm (Kirkpatrick S, Gelatt C D, Jr., Vecchi M P. Optimization by Simulated Annealing. Science 1983; 220(4598):671-680) was used to optimize both inter-pulse delays and the relative pulse amplitudes. In all optimization approaches, a $B_1$ region was set for optimization, roughly centered on the $B_1$ required for a 90° pulse with the chosen $HS_1$ pulse. This region comprised an N-1 fold variation in $B_1$, where N is the number of pulse repetitions. $B_1$ min and $B_1$ max are the boundaries for the optimization interval, with % $B_1$ values and the coefficients normalized to the $B_1$ for a 90° response ($\gamma B_1/2\pi$=37

Hz). The optimization target was to minimize the resultant absolute $M_z$. To better optimize the central part of the $B_1$ range, a weight function, $w(x)=\exp(-p \cdot x_p)$, was applied to the residual $M_z$ values calculated for the optimization with p=24 and $-1<x(B_1)<1$ to scale the $B_1$ range. Initial values were set as unity for all pulses or as a ramp function or as a sech function. The latter served as a good starting point for sequences with larger numbers of pulses.

As shown in Table 1, for the five- and seven-pulse sequence, the coefficients do not vary much with $T_1$ as they do for the three-pulse sequence. It was found that a five- or seven-pulse sequence, optimized for a particular $T_1$, was also very close to optimal for other $T_1$ values. The coefficients of the three-pulse sequence are somewhat more variable with regard to $T_1$ differences. The values in Table 1 are relative amplitude values. The $B_1$ range covered by a sequence with a particular RF pulse shape depends on the absolute RF powers of that pulse.

Magnetic resonance pulse sequences with optimized pulse amplitudes according to Table 1 were then tested with numerical simulations of the Bloch equations. The Bloch simulations were performed on small pulse steps (minimum 500 steps per pulse), and relaxation effects during the pulses were included. Three or more pulse repetitions were each followed by zeroing the transverse magnetization to simulate crusher gradients and a short free-precession to simulate the relaxation during the crusher and final pre-excitation delay. For comparison with existing suppression sequences, similar simulations were performed with sin c-gauss pulses (five-lobe sin c pulse apodized with a Gaussian function). For these simulations, the relative amplitudes required to yield the flip angles and delays prescribed for WET or VAPOR water suppression (Ws) were determined, using the same RF pulse durations used for the adiabatic pulses.

Figure 9:
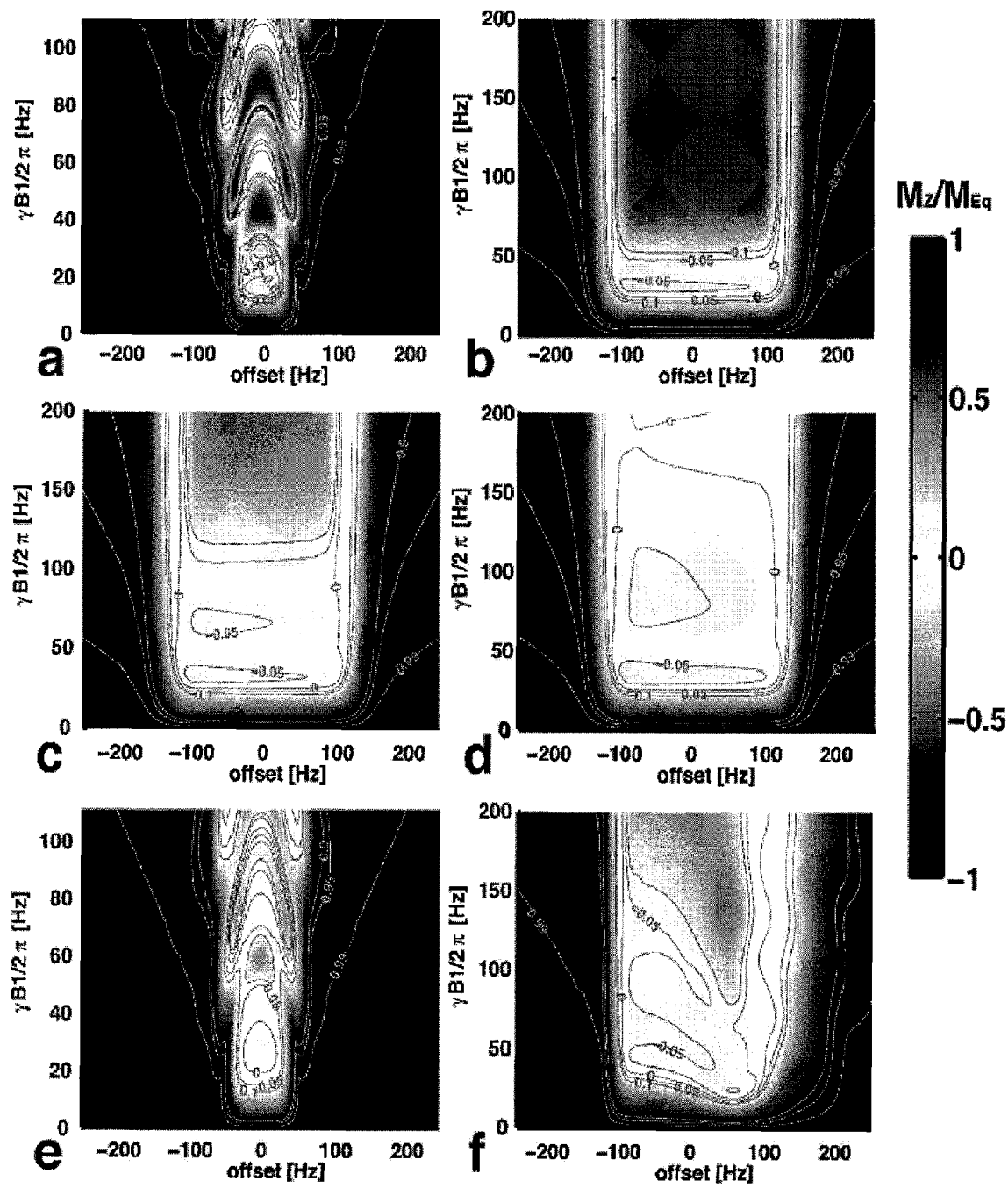
FIG. 9 shows the simulated frequency responses of two reference RF pulses and another four more RF pulses obtained according to some embodiments of the current invention.

FIG. 9 shows the simulated frequency responses of two reference RF pulses and another four more RF pulses obtained according to some embodiments of the current invention. In FIG. 9, the suppression pulse sequences optimized for $T_1=0.75$ s are compared with WET sequences (as reference RF pulses) using a sin c-gauss pulse. The sin c-gauss BW was adjusted to achieve the same sequence duration. For each point in all the simulations with adiabatic pulses shown in FIG. 9, the amplitude of the RF pulses was the multiplication product of coefficients from Table 1, and the B1 values on the Y-axis.

FIG. 9 displays residual magnetization (Mz/Meq) on a grayscale for signals with $T_1=0.75$ and $T_2=250$ ms as a function of offset frequency and local $B_1$. In (a), the response is shown for a three-pulse WET sequence with a 67.5 ms 83 Hz BW sin c-gauss pulse. In (b), the response is shown for optimized adiabatic pulse saturation sequences using a 67.5 ms $HS_1$ pulse with three pulse repetitions. In (c) and (d), the responses are shown, respectively, for five repetitions and seven repetitions. In (e), the response is shown for the sin c-gaus pulse in a VAPOR suppression sequence. In (f), the response is shown for the five-pulse sequence of (b), with the $HS_1$ pulse replaced by a hyper-pulse (sharp end $HS_{0.5}$, blunt end $HS_{2.5}$ ¼ of the pulse time, both μ=5 truncated at 2% duration, 67.5 ms, and a nominal BW of 250 Hz). The Y-axes in (a) and (e) have a different scale compared to the rest of the plots. This is because the $B_1$ range used in the simulations was scaled to the $B_1$ required for an effective 90° flip angle (RF90) and for the sin c-gaus this RF90 is lower by a factor of about 0.55 compared to the $HS_1$ and hyper-pulse.

The range of $B_1$ with good suppression for the optimized three $HS_1$ pulses sequence is comparable to that of the WET sequence with sin c-gauss pulses as shown in (a) and (b). Nevertheless, the off-resonance response of the $HS_1$ is better. The $B_1$ working range vastly improves when the number of pulses is increased to five or seven, as shown in (c) and (d). The VAPOR sequence with sin c-gauss pulses has a response shown in (e), which is comparable to that of a five-pulse $HS_1$ sequence. However, at higher $B_1$, the off-resonance response deteriorates. To improve the sharpness of transition for the adiabatic pulses, the adiabatic pulse in the five-pulse sequence was replaced by a hyper-pulse as discussed above, with the results shown in (f). The results in (f) are clearly superior to that shown in (e), indicating applications in water signal suppression for in-vivo H-MRS and observation of metabolites with chemical shifts below that of water.

Signal suppression with adiabatic pulses was also tested in a modified point-resolved spectroscopy (PRESS) spectroscopy sequence (Bottomley P A. Spatial localization in NMR spectroscopy in vivo. Ann N Y Acad Sci 1987; 508:333-348) on a 3 T MR scanner (Magnetom Trio-Tim System, Siemens Medical Solutions Erlangen, Germany). The modified sequences allowed switching between a WET water suppression sequence with a sin c-gauss pulse (original sequence implementation) and three-, four-, or five-pulse suppression sequences with minimal inter-pulse delays and amplitudes optimized for signal suppression with adiabatic pulses. The RF pulse amplitude of the suppression pulses could be scaled as a group with a user-controlled group scaling factor (GSF) to examine RF amplitude dependence of the suppression schemes. For measurement of the response profiles of the suppression schemes, a low amplitude gradient pulse was switched on during the suppression pulses and during readout to create a frequency profile over the signal from the PRESS localized volume. For dual-band pulses, the profile gradients were scaled to create a field of view three times the PRESS voxel size of 4 cm and a suppression PBW of ⅒ of the PRESS voxel size. Thus, the profiles show a one-dimensional projection of the PRESS volume selection superimposed on the response profile of the suppression pulse. After all MRS experiments on phantoms, the $T_1$ of the phantom was measured with a series of six single-slice inversion recovery MR images (128×128, 20 mm slice, minimum echo turbo-SE, TI=23, 100, 200, 400, 800, 1200, and 2400 ms, TR=6000 ms).

Figure 10:
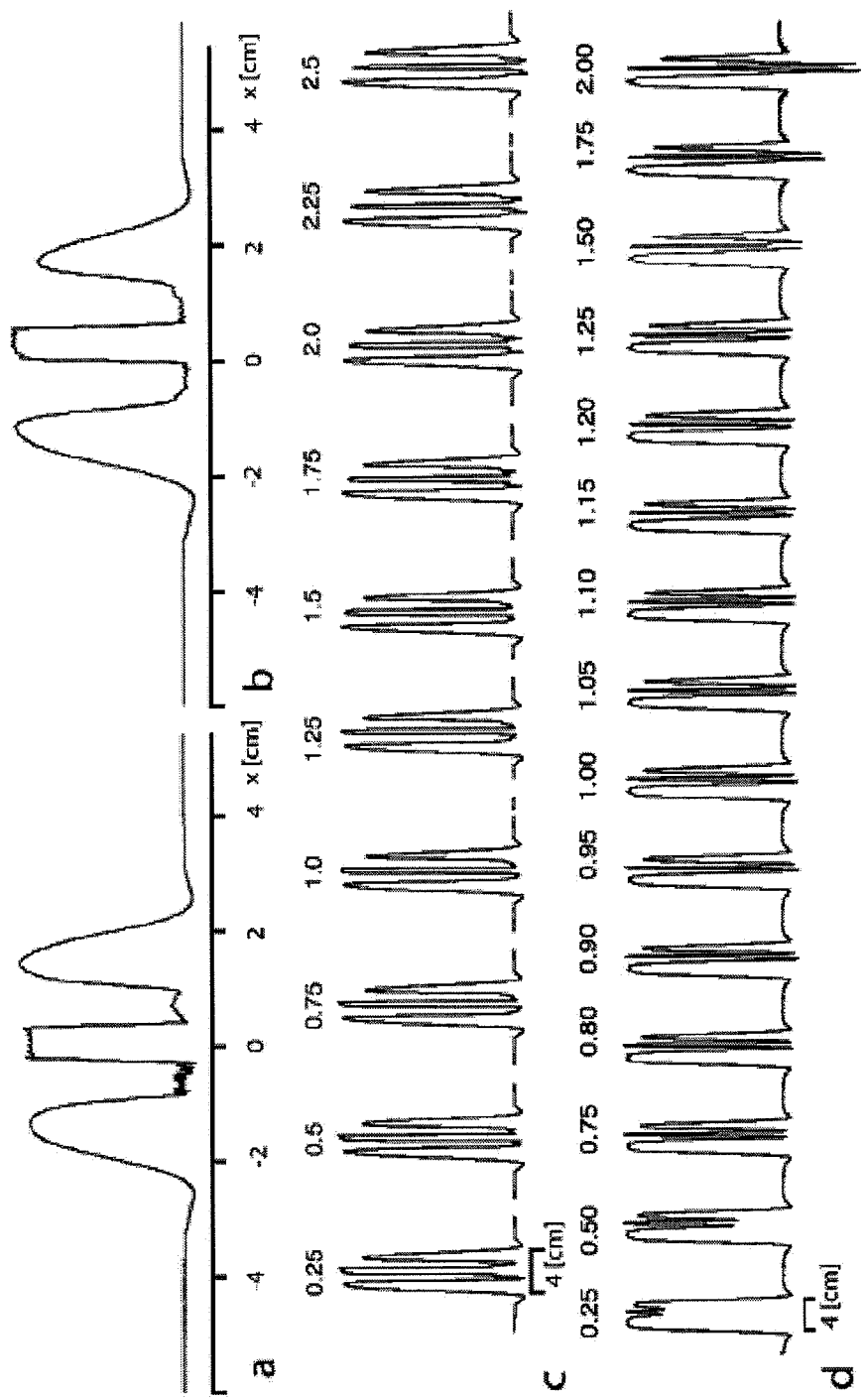
FIG. 10 shows measured results from a phantom using RF pulses according to some embodiments of the invention.

FIG. 10 shows measured results from a phantom using RF pulses according to some embodiments of the invention. Spatially selective profiles of the dual-band water fat suppression (WFS) sequences were obtained using the optimized coefficients of Table 1 for $T_1=0.75$ s. The dual-band WFS pulse length was 45.3 ms for a 350 Hz pass-band width. Profiles were recorded with a modified PRESS sequence, with profile gradients on during the suppression sequence and readout at 8 kHz receiver BW and 8 k points. Each profile here is a projection of the signal from the PRESS selected volume on the RF profile readout axis. The RF pulse amplitudes are the pulse amplitude required for a 90° effective flip angle multiplied by the coefficients in Table 1 and the group scaling factor (GSF). In (a) and (b), profiles are shown, respectively for the three pulse sequence and the seven pulse sequence, each with the GSF set to 1. In (c), profiles for the seven pulse sequence are shown with different GSF as indicated above each profile. The results were obtained from a doped water phantom with a $T_1$ of 1.25 s. In (d), profiles of the three-pulse sequence are shown with different GSF (as indicated above each profile) on a different doped water phantom with a $T_1$ of 0.45 s.

In FIG. 10, spatially selective profiles were recorded of a 4×4×4 cm PRESS volume selection centered on the phantom. In (a)-(c), the doped water phantom has a $T_1$ of 1.25 s. With the three and seven pulses, shown respectively in (a) and (b), a good response is observed for both the water and fat suppression band (with the GSF set to 1). According to (c), with the seven-pulse sequence, a good consistent response is seen with GSFs between 0.25 and 2.25. The $B_1$ insensitivity was also tested on a different water doped phantom with a $T_1$ of 0.45 s for the three-pulse sequence, with the results shown in (d). Here the response is good for a GSF between 0.75 and 1.5. The results demonstrate the $B_1$ insensitivity of the RF pulses obtained according to some embodiments of the current invention. Further, the $B_1$ insensitivity is robust within a range of physiologically relevant $T_1$ values.

Figure 11:
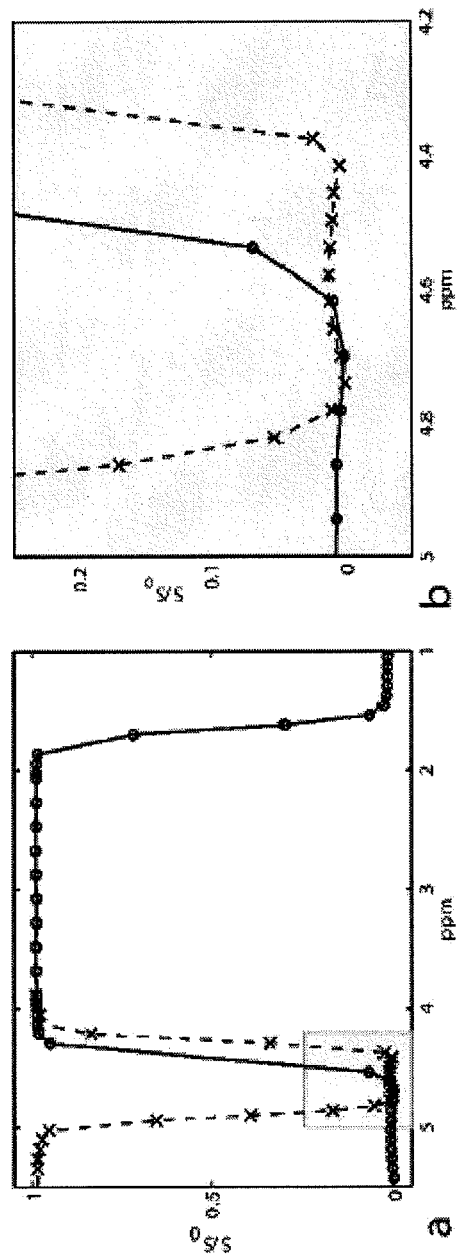
FIG. 11 compares spectral profiles measured from a phantom using WET suppression scheme and a suppression scheme according to some embodiments of the current invention.

FIG. 11 compares spectral profiles measured from a phantom using WET suppression scheme and a suppression scheme according to some embodiments of the current invention. Spectral profiles of the WET suppression scheme and the three pulses dual-band WFS sequence were obtained using the optimized coefficients of Table 1 for $T_1$ of 0.75 s. The dual band WFS pulse has a duration of 45.3 ms for a PBW of 350 Hz, compared to the WET water suppression sequence with a 43.8 ms three lobe sin c-gauss pulse and a BW of 65 Hz (BWTP=2.85). In (a), absolute integral of the water signal (4.68-4.72 ppm) is plotted as a function of water suppression offset frequency. Spectra were recorded using a standard PRESS localization sequence (without a profile gradient) with a 1.5 kHz bandwidth and 1 k points and zero filled to 2 k points. The water signal with the suppression sequence turned off (denoted as $S_0$) was used to determine zero order phase correction for signal normalization of the integrated water signals (denoted as S). The $T_1$ of the phantom, determined with inversion recovery (IR) $_1$H-MRI was 1.25 s. The dual-band pulse length was 45 ms for a 350 Hz pass-band width. Integrated absolute peak area of the water peak, $S/S_0$ is plotted as a function of the water suppression offset frequency for the dual band pulse (solid line, o) and for a standard WET sequence with a 45 ms 35 Hz BW sin c-gauss pulse (dashed line, x). In (b), an enlarged plot of the gray area in (a) is shown around 4.7 ppm corresponding to the chemical shift of water.

FIG. 11 demonstrates that the dual band WFS pulse sequence does indeed have a sharp pass-band, leaving all signals in the metabolite region between 2 and 4.2 ppm virtually unaffected. For water suppression at 4.7 ppm, the definition is comparable to that of the sin c-gaus WET sequence on the metabolite side, but continues to suppress for shifted or broadened water signals at higher chemical shifts. Thus, the dual band pulse response profile was confirmed in detail by measurement of the residual water signal on a phantom with $T_1$ of 1.25 s.

Using the same modified PRESS sequence described above, the dual-band WFS scheme was tested on two healthy human volunteers. The study protocol was approved by the Johns Hopkins University Institutional Review Board and all subjects gave written, informed consent. Several, single-voxel $_1$H-PRESS spectra were recorded in two volunteers on locations close to the skull, a location likely to lead to contaminating signals from lipids of the skull and subcutaneous fat. The dual-band pulse PBW was optimized and the RF power and water suppression offset frequencies were varied for both the dual-band schemes and the WET water suppression.

Figure 12:
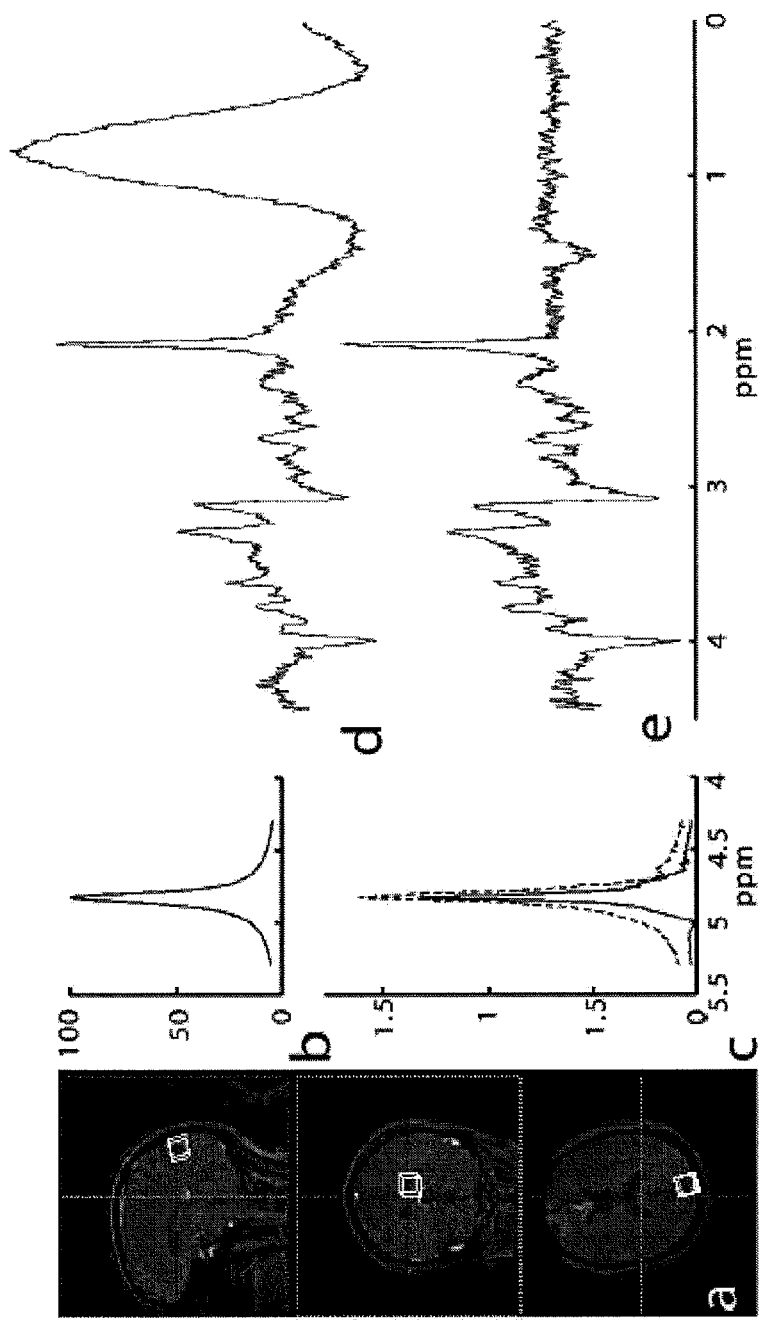
FIG. 12 compares results from in-vivo 1H-MRS of a human brain using WET water suppression and a dual-band, water-fat suppression scheme according to some embodiments of the current invention.

FIG. 12 compares results from in-vivo $_1$H-MRS of a human brain using WET water suppression and a dual-band water-fat suppression scheme according to some embodiments of the current invention. Single-voxel spectra recorded with PRESS (TE/TR=135/1800, 64 averages). In (a), scout images in three planes indicate the position of a 2 cm cubed voxel close to the skull. In (b), the magnitude of water signal without suppression is shown. In (c), the magnitudes of water signal are shown at a 100× magnification scale, using a WET water suppression sequence (dashed line) having a sin c-gauss pulse (BW of 35 Hz) and using a three-pulse suppression sequence with dual-band pulses (35 ms, PBW of 350 Hz) optimized for suppression at a $T_1$ of 0.75 s (solid line). In (d), real spectrum of the metabolites and lipids with WET suppression is shown. In (e), real spectrum of the metabolites and lipids with dual-band suppression is plotted with the same scale as in (d). Both spectra of (d) and (e) were zero-order phase-corrected with the same parameters to yield an in-phase NAA peak.

As shown in FIG. 12, the three-pulse sequence, with coefficients as listed in Table 1 for $T_1$=0.75 s, proved to be at least as effective for water suppression as the WET sequence with sine-gauss pulses. The WFS sequence with dual-band pulses also eliminated most of the fat signal as shown in the spectra in (e). The residual water peak in (c) appears smaller and narrower for the WFS sequence. This is likely a beneficial effect of the wider suppression band of the pulses used in that sequence.

Figure 13:
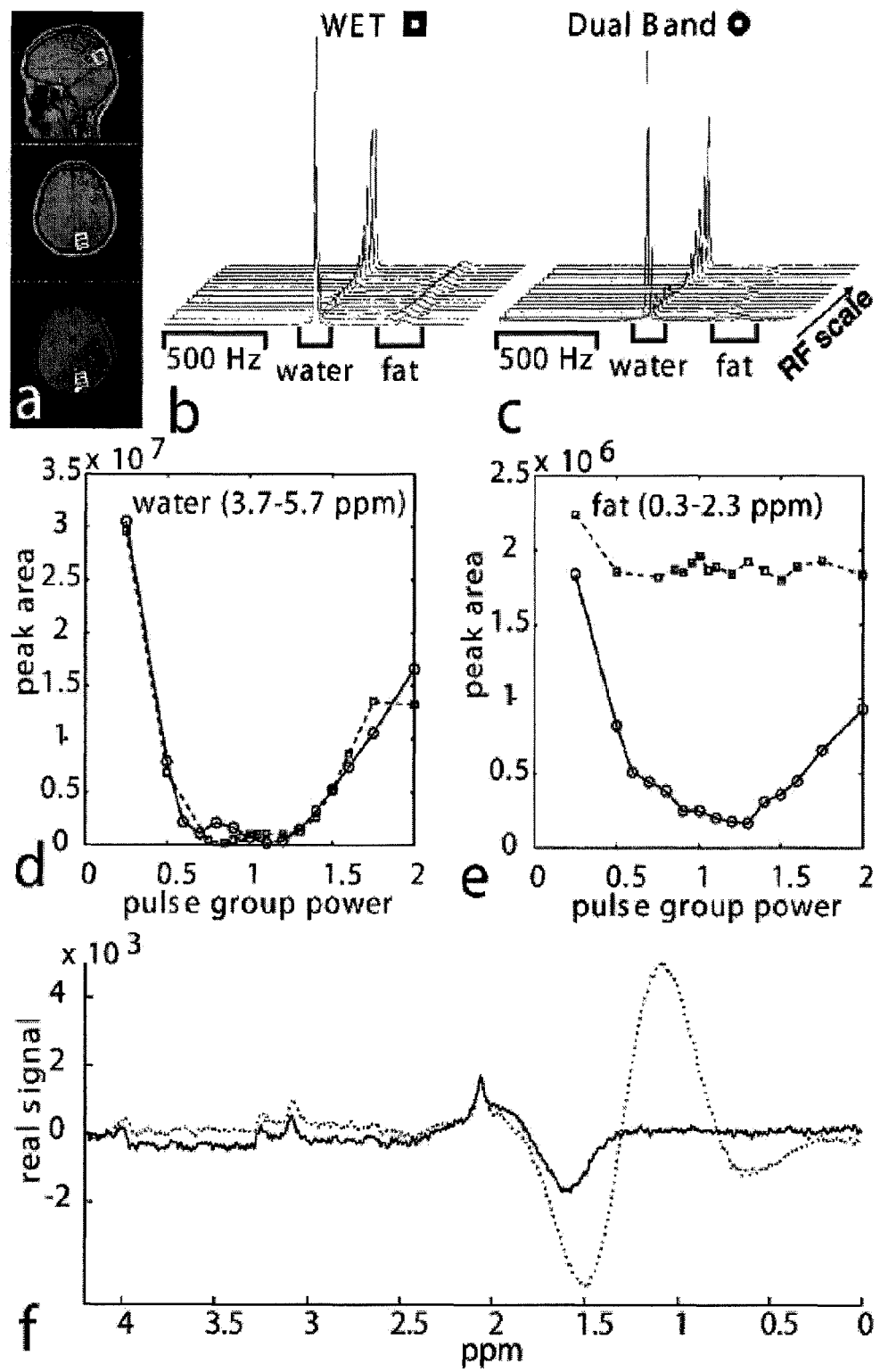
FIG. 13 illustrates in-vivo $B_1$ insensitivity of a dual-band, water-fat suppression scheme according to some embodiments of the current invention in comparison with a conventional WET water suppression scheme.

FIG. 13 illustrates in-vivo $B_1$ insensitivity of a dual-band, water-fat suppression scheme according to some embodiments of the current invention in comparison with a conventional WET water suppression scheme. In-vivo tests of $B_1$ insensitivity were conducted using a WET water suppression and a dual-band water/fat suppression for $_1$H-MRS of a human brain. Single-voxel PRESS spectra (TE/TR=135/1800) from a 2×2×2 cm voxel close to the skull, similar in placement to that shown in FIG. 12 were recorded with eight averages each, with the RF amplitudes of the water suppression scheme varied. The RF GSF were 0.2, then 0.5 to 1.5, in increasing steps of 0.1, 1.7, and 2. In (a), three-plane scout images indicate the voxel position. In (b), stacked plot is shown for real spectra recorded with a three-pulse WET water suppression using sin c-gauss pulses. In (c), stacked plot is shown for real spectra recorded with a three-pulse dual-band water/fat suppression sequence. In (d), absolute integral are shown for the water peak (3.7-5.7 ppm) obtained from WET (open squares) and dual-band WFS (open circles) after second-order spline baseline correction. In (e), absolute integral are shown for the fat peaks (0.3-2.3 ppm) obtained from WET (open squares) and dual-band (open circles) pulse sequences. In (f), phase corrected real spectra (four averages) are shown using WET (dashed line) and dual-band WFS (solid line) pulse sequences. Both pulse sequences have a group amplitude scaling factor (GSF) of 1. Zero and first order phase corrections in both spectra were based on maximizing the NAA absorption peak and the peaks between 3 and 3.5 ppm in the real spectrum with dual-band WFS.

The spectra shown in the stacked plots of FIG. 13 were recorded with a series of group amplitude scaling factors (GSF) of 0.25, 0.5, 0.6 . . . 1.5, 1.75, and 2 for the entire suppression sequence to test the extent of the $B_1$-insensitivet response of the suppression sequences. The WET sequence with sin c-gauss pulses was compared with the optimized three-pulse sequence with dual-band adiabatic pulses. The spectral regions of interest include water (3.7-5.7 ppm) and fat (0.3-2.3 ppm). For water suppression, both sequences again showed comparable results. The spectra with a GSF of 0.2 had a seriously distorted baseline from the large residual water signal. This probably added to the fat integrals of these spectra even though a linear baseline correction was applied prior to all peak area integrations. Other than that, the fat signal in the WET spectra is fairly constant, whereas the WFS spectra show a reasonably good fat suppression with GSF from 0.5 to 1.5. Thus, dual band pulse WFS was achieved in-vivo without a loss of water suppression quality. Furthermore, the spectra in (f) of FIG. 13 demonstrate a more significant reduction of the broad lipid peak using a dual band WFS scheme according to some embodiments of the invention. In this volunteer, the contaminating lipid signal was much broader and closer to the metabolite frequencies than that in the spectra of FIG. 12. Although not completely suppressed by the dual band suppression, which was set to cut off frequencies below 1.2 ppm, the lipid signal is reduced by an order of magnitude in the dual-band WFS spectrum relative to the WET spectrum.

Examples of dual-band adiabatic pulses and their applications are presented, demonstrating some of the myriad possibilities for using multi-band selective pulses. With these examples, adiabatic dual-band pulses are shown to be versatile, effective, and easy to implement for a wide range of applications in MRS or MRI.

Some embodiments of the current invention may allow a reduction in deposited RF power when multiple frequency bands or regions need to be suppressed by achieving multi-band responses with a single pulse rather than a series of consecutive pulses.

In some embodiments of the current invention, the adiabatic dual-band pulses may not be truly adiabatic, but they are capable of $B_1$ field-independent, frequency-selective inversion over limited ranges of $B_1$ field strengths. For many applications, this may be all that is required, because $B_1$ inhomogeneities of most transmit coils do not vary too much over the volume of interest (VOI). In addition, these $B_1$ inhomogeneities should not vary too much if spin echo sequences with conventional pulses are used. Moreover, if the pulses are to be used for selective saturation by selective excitation, the $B_1$-independent inversion properties may not be useful. Even with the well-known adiabatic HS pulses, a $B_1$-independent excitation response can be achieved only with optimized multi-pulse experiments. The $B_1$-independent response range is then roughly proportional to the number of pulses, which may require longer pulses and/or larger SAR. However, the main attractiveness of using adiabatic pulses is because their profiles tend to be much more $B_1$-insensitive than the profiles of non-adiabatic pulses.

The experiments presented in this paper show that dual band pulses can yield effective signal suppression in multi pulse suppression sequences with optimized RF pulse amplitude coefficients. The robustness towards variations in $B_1$ and $T_1$ increases with the number of pulses used, but even three-pulse sequences show consistent response within an almost two-fold variation of $B_1$. Signal suppression with saturation pulses is likely to work better for longer $T_1$, but the three-pulse dual band WFS sequence, optimized for $T_1$=0.75 s, works well on a phantom with a $T_1$ of less than 0.5 s and on fat signals in vivo. Thus, these multi-pulse sequences with optimized RF amplitude coefficients can achieve excellent of signal suppression in experiments with both $B_0$ and $B_1$ field inhomogeneities.

Selective multi-band adiabatic pulses can be optimized for specific tasks in ways that are impossible with non-adiabatic pulses designing the inversion or suppression bands to be different in profile, width, and amplitude. Relative contributions of each component can be scaled, either to match the minimum $B_1$ field at which each inversion band becomes pseudo-adiabatic, or to fine-tune individual flip-angles, which might prove useful in spectral editing.

This design flexibility allows compensations for timing and $T_1$ differences if the pulse is to be used as a suppression pulse at sub-adiabatic RF amplitudes. Specifically, for applications where the pulses are used for combined water and fat suppression in $_1$H-MR spectroscopy or Inversion-Recovery with ON-resonant water suppression (IRON) MRI (Stuber M, Gilson W D, Schar M, Kedziorek D A, Hofmann L V, Shah S, Vonken E J, Bulte J W, Kraitchman D L. Positive contrast visualization of iron oxide-labeled stem cells using inversion-recovery with ON-resonant water suppression (IRON). Magn Reson Med 2007; 58(5):1072-1077), dual-band pulses with unequal bandwidths and amplitudes can be advantageous to accommodate the different longitudinal relaxation rates and peak widths of water and fat. Two separate methods are shown for the use of dual-band adiabatic pulses for efficient signal suppression, but other applications can be found such as inversion pulses for blood flow measurements or localization schemes. With the design freedom demonstrated here, quasi-adiabatic multi-band pulses can be optimally designed and implemented for many different MR applications.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

APPENDIX A

The on-resonance $M_z/M_{Eq}$ of a HS1 pulse was derived from Eq. 17 in ref. (14) as follows:

$$\frac{M_z}{M_{Eq}} = \tanh\left(\frac{\pi\Delta\omega}{2\beta} + \frac{\pi\mu}{2}\right) \cdot \tanh\left(\frac{\pi\Delta\omega}{2\beta} - \frac{\pi\mu}{2}\right) + \cos\left[\pi \cdot \sqrt{\left(\frac{\Omega_o}{\beta}\right)^2 - \mu^2}\right] \cdot \text{sech}\left(\frac{\pi\Delta\omega}{2\beta} + \frac{\mu}{2}\right) \cdot \text{sech}\left(\frac{\nu\Delta\omega}{2\beta} - \frac{\mu}{2}\right) \quad [A1]$$

In ref. (14) $\Omega_0$ is the RF amplitude=$\gamma B1$ [rad/s] and $\pi \cdot BW = \beta \cdot \mu$, so that $$\frac{\Omega_o}{\beta} = \frac{\gamma \cdot B1 \cdot \mu}{BW \cdot \pi}$$

$$\frac{M_z}{M_{Eq}} = \tanh\left(\frac{\pi\Delta\omega}{2\beta} + \frac{\pi\mu}{2}\right) \cdot \tanh\left(\frac{\pi\Delta\omega}{2\beta} - \frac{\pi\mu}{2}\right) + \cos\left[\pi \cdot \mu\sqrt{\left(\frac{\gamma \cdot B1}{BW \cdot \pi}\right)^2 - 1}\right] \cdot \text{sech}\left(\frac{\pi\Delta\omega}{2\beta} + \frac{\mu}{2}\right) \cdot \text{sech}\left(\frac{\nu\Delta\omega}{2\beta} - \frac{\mu}{2}\right) \quad [A2]$$

setting the off resonance $\Delta\omega$ to zero and using $\tan h(-z) = -\tan h(z)$ and $\text{sech}(z) = \text{sech}(-z)$ leaves:

$$\frac{M_z}{M_{Eq}} = -\tanh^2\left(\frac{\pi\mu}{2}\right) + \cos\left[\pi \cdot \mu\sqrt{\left(\frac{\gamma \cdot B1}{BW \cdot \pi}\right)^2 - 1}\right] \cdot \text{sech}^2\left(\frac{\pi\mu}{2}\right) \quad [A3]$$

because $\tan h^2(z) = 1/\cos h^2(z) + 1$, $\text{seqh} = 1/\cos h(z)$ and $\cos h(z) = \cos h(-z)$ this is equivalent to:

$$\frac{M_z}{M_{Eq}} = \frac{1}{\cosh^2\left(\frac{\pi\mu}{2}\right)} + 1 + \cos\left[\pi \cdot \mu \sqrt{\left(\frac{\gamma \cdot B1}{BW \cdot \pi}\right)^2 - 1}\right] \cdot \frac{1}{\cosh^2\left(\frac{\pi\mu}{2}\right)} \quad [A4]$$

now we can use $\cos h^2(2z) = 2\cos h^2(z) - 1$ to simplify to:

$$\frac{M_z}{M_{Eq}} = \frac{1 - \cosh(-\pi \cdot \mu) + 2\cos\left[\pi \cdot \mu \sqrt{\left(\frac{\gamma \cdot B1}{BW \cdot \pi}\right)^2 - 1}\right]}{1 + \cosh(-\pi \cdot \mu)} \quad [A5]$$

It is important that the cosine of complex numbers can be calculated using Eq. 2 to get a meaningful result when $$\left(\frac{\gamma \cdot B1}{BW \cdot \pi}\right)^2 < 1 \quad [A6]$$

I claim:

1. A magnetic resonance imaging (MRI) system, comprising:
a magnetic resonance imaging scanner comprising:
a main magnet providing a substantially uniform main magnetic field $B_0$ for a subject under observation; and
a radio frequency (RF) coil configured to irradiate a radio frequency (RF) pulse into a region of interest of said subject under observation,
wherein said RF pulse is a resultant pulse including a summation of a first base pulse comprising a first adiabatic pulse and a second base pulse comprising a second adiabatic pulse,
wherein said RF pulse selectively suppresses magnetic resonance signals from more than one chemical component or more than one spatial region within said region of interest of said subject under observation, and
wherein said first adiabatic pulse is characterized by a first amplitude modulation function and a first frequency modulation function, and said second adiabatic pulse is characterized by a second amplitude modulation function and a second frequency modulation function.

2. The MRI system according to claim 1, wherein the at least one of the first and second adiabatic pulses is a form of a hyperbolic-secant (HS) pulse.

3. The MRI system according to claim 1, wherein at least one of said first and second base pulses further comprises a blunt pulse to form a hyper-pulse.

4. The MRI system according to claim 3, wherein the blunt pulse is a Numerically-Optimized-Modulation (NOM) pulse or a HS pulse with an order above 2.

5. The MRI system according to claim 3, wherein at least one of said first and second bases pulses has a first bandwidth and time product (BWTP), and said blunt pulse has a second bandwidth and time product (BWTP) that is substantially smaller than said first BWTP.

6. The MRI system according to claim 1, wherein said RF pulse further comprises at least a new instance of at least one of said base pulses with a new scaling factor for said amplitude modulation or said frequency modulation.

7. The MRI system according to claim 1, wherein at least one of said base pulses is a hyper-pulse.

8. The MRI system according to claim 1, wherein said more than one chemical components comprises at least one of water, triacylglycerol, N-acetyleaspartase (NAA), or combinations thereof.

9. The MRI system according to claim 1, wherein said subject is a human, an animal, a phantom, a sample, or combinations thereof.

10. The MRI system according to claim 1, further comprising:
a signal processing unit in communication with said magnetic resonance imaging scanner to receive a plurality of magnetic signals from said region of interest in response to said RF pulse.

11. The MRI system according to claim 10, wherein said signal processing unit performs spectral editing for said received magnetic resonance signals.

12. The MRI system according to claim 1, wherein said magnetic resonance imaging scanner further comprises a gradient system to generate spoiler gradients to dephase said MR signals from said more than one chemical component or said more than one spatial region within said region of interest of said subject under observation.

13. A magnetic resonance imaging (MRI) system, comprising:
a magnetic resonance imaging scanner comprising:
a main magnet providing a substantially uniform main magnetic field B0 for a subject under observation; and
a radio frequency (RF) coil configured to irradiate a radio frequency (RF) pulse into a region of interest of said subject under observation,
wherein said RF pulse comprises a base pulse comprising an adiabatic pulse having a first bandwidth the product (BWTP),
wherein said RF pulse selectively suppresses magnetic resonance signals from more than one chemical component or more than one spatial region within said region of interest of said subject under observation, and
wherein said adiabatic pulse is characterized by an amplitude modulation function and a frequency modulation function,
wherein said base pulse further comprises a blunt pulse to form a hyper-pulse, and
wherein the RF pulse further comprises a time-reversed instance of said hyper-pulse.

14. A magnetic resonance imaging (MRI) system, comprising:
a magnetic resonance imaging scanner comprising:
a main magnet providing a substantially uniform main magnetic field B0 for a subject under observation; and
a radio frequency (RF) coil configured to irradiate a radio frequency (RF) pulse into a region of interest of said subject under observation,
wherein said RF pulse comprises a base pulse comprising an adiabatic pulse having a first bandwidth time product (BWTP),
wherein said RF pulse selectively suppresses magnetic resonance signals from more than one chemical component or more than one spatial region within said region of interest of said subject under observation, and
wherein said adiabatic pulse is characterized by an amplitude modulation function and a frequency modulation function, and
wherein said magnetic resonance imaging scanner further comprises timing circuits to generate inversion delays to attenuate said MR signals from said more than one chemical component or said more than one spatial region within said region of interest of said subject under observation.

15. A method for magnetic resonance imaging or spectroscopy using a radio frequency (RF) pulse to be transmitted by a RF coil into a region of interest of a subject under observation in a magnetic resonance scanner having a main magnet, the method comprising:
receiving parameters relating to magnetic resonance spectral locations corresponding to more than one chemical component or more than one spatial region within said region of interest;
choosing at least two adiabatic pulses to form at least two base pulses wherein the at least two adiabatic pulses have frequency responses which have notches at said spectral locations;
combining the at least two adiabatic pulses into said RF pulse;
transmitting said RF pulse to selectively suppress magnetic resonance signals from said magnetic resonance spectral locations corresponding to said more than one chemical component or said more than one spatial region within said region of interest; and
obtaining a spectrum measurement or image from said region of interest.

16. The method according to claim 15, wherein at least one of the adiabatic pulses is a form of a hyperbolic-secant (HS) pulse.

17. The method according to claim 15, further comprising:
adding a blunt pulse to at least one of said adiabatic pulses to generate a hyper-pulse.

18. The method according to claim 17, wherein the blunt pulse is a Numerically-Optimized-Modulation (NOM) pulse.

19. The method according to claim 17, wherein said notches are spectrally asymmetric.

20. The method according to claim 17, wherein said notches have identical spectral widths.

21. The method according to claim 17, wherein said notches have non-identical spectral widths.

22. The method according to claim 17, further comprising:
adding to said RF pulse a time-reversed instance of said hyper-pulse.

23. The method according to claim 22, wherein said time-reversed instance is scaled differently than said hyper-pulse.

24. The method according to claim 15, further comprising:
adding at least one new instance of at least one of said base pulses with a new scaling factor for said amplitude modulation function or said frequency modulation function.

25. The method according to claim 24, further comprising:
minimizing residual transverse magnetization corresponding to said more than one chemical component or said more than one spatial region within said region of interest of said subject under observation.

26. The method according to claim 25, wherein said minimizing takes into account of at least one of spatial $B_1$ variations over said region of interest and $T_1$ relaxation effect when said RF pulse is being transmitted to said region of interest.

27. The method according to claim 15, wherein said transmitting is applied immediately preceding a read-out gradient pulse.

28. The method according to claim 15, wherein said transmitting selectively refocuses said MR signals from said more than one chemical components or said more than one spatial regions within said region of interest of said subject under observation.

29. The method according to claim 15, wherein said transmitting suppresses outer volume signals.

30. A computer-readable medium containing software, which software when executed by a computer, causes the computer to implement the method according to claim 15.

* * * * *